US012115009B2

(12) United States Patent
Sun et al.

(10) Patent No.: US 12,115,009 B2
(45) Date of Patent: *Oct. 15, 2024

(54) POSITRON EMISSION TOMOGRAPHY IMAGING SYSTEM AND METHOD

(71) Applicant: SHANGHAI UNITED IMAGING HEALTHCARE CO., LTD., Shanghai (CN)

(72) Inventors: Youjun Sun, Shanghai (CN); Tao Feng, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/179,327

(22) Filed: Mar. 6, 2023

(65) Prior Publication Data

US 2023/0210477 A1 Jul. 6, 2023

Related U.S. Application Data

(63) Continuation of application No. 15/970,911, filed on May 4, 2018, now Pat. No. 11,596,366.

(30) Foreign Application Priority Data

May 4, 2017 (CN) .......................... 201710308089.1

(51) Int. Cl.
*A61B 6/03* (2006.01)
*A61B 6/00* (2024.01)
(Continued)

(52) U.S. Cl.
CPC ............ *A61B 6/037* (2013.01); *A61B 6/0487* (2020.08); *A61B 6/5235* (2013.01);
(Continued)

(58) Field of Classification Search
None
See application file for complete search history.

(56) References Cited

U.S. PATENT DOCUMENTS

2004/0209237 A1* 10/2004 Flewelling ........... A61B 5/7264
600/315
2004/0258286 A1 12/2004 Salla et al.
(Continued)

FOREIGN PATENT DOCUMENTS

CN 105078495 A 11/2015

OTHER PUBLICATIONS

First Office Action in Chinese Application No. 201710308089.1 mailed on Oct. 8, 2019, 17 pages.
(Continued)

*Primary Examiner* — Katherine L Fernandez
*Assistant Examiner* — Farouk A Bruce
(74) *Attorney, Agent, or Firm* — METIS IP LLC

(57) ABSTRACT

A method and system for determining a PET image of the scan volume based on one or more PET sub-images is provided. The method may include determining a scan volume of a subject supported by a scan table; dividing the scan volume into one or more scan regions; for each scan region of the one or more scan regions, determining whether there is a physiological motion in the scan region; generating, based on a result of the determination, a PET sub-image of the scan region based on first PET data of the scan region acquired in a first mode or based, at least in part, on second PET data of the scan region acquired in a second mode; and generating a PET image of the scan volume based on one or more PET sub-images.

7 Claims, 12 Drawing Sheets

(51) Int. Cl.
*A61B 6/04* (2006.01)
*A61B 6/46* (2024.01)
*G06T 11/00* (2006.01)

(52) U.S. Cl.
CPC ............ *A61B 6/5264* (2013.01); *A61B 6/541* (2013.01); *A61B 6/545* (2013.01); *G06T 11/005* (2013.01); *A61B 6/032* (2013.01); *A61B 6/4417* (2013.01); *A61B 6/461* (2013.01); *A61B 6/5205* (2013.01); *A61B 6/563* (2013.01); *G06T 2207/10104* (2013.01); *G06T 2211/412* (2013.01)

(56) References Cited

U.S. PATENT DOCUMENTS

| | | |
|---|---|---|
| 2005/0175140 A1 | 8/2005 | Tsujii |
| 2006/0120586 A1 | 6/2006 | Iatrou et al. |
| 2009/0296998 A1 | 12/2009 | Fox et al. |
| 2010/0067765 A1 | 3/2010 | Buther et al. |
| 2010/0290683 A1 | 11/2010 | Demeester et al. |
| 2012/0330154 A1 | 12/2012 | Beasley et al. |
| 2013/0113938 A1* | 5/2013 | Miyaki ................ A61B 8/0891 348/163 |
| 2014/0148684 A1 | 5/2014 | Foo et al. |
| 2014/0243649 A1 | 8/2014 | Rocque et al. |
| 2015/0021488 A1 | 1/2015 | Stearns |
| 2015/0227781 A1* | 8/2015 | Morishita ............. G06V 40/40 382/118 |
| 2016/0128664 A1 | 5/2016 | Manjeshwar et al. |
| 2016/0163042 A1 | 6/2016 | Wollenweber et al. |
| 2016/0163095 A1 | 6/2016 | Wollenweber |
| 2017/0020466 A1 | 1/2017 | Moulin et al. |

OTHER PUBLICATIONS

The Third Office Action in Chinese Application No. 201710308089.1 mailed on May 25, 2022, 24 pages.

* cited by examiner

Relative position of a center of mass corresponding to a PET image of a scan region B  Time Period
(the nth 100 microseconds)

POSITRON EMISSION TOMOGRAPHY IMAGING SYSTEM AND METHOD

CROSS-REFERENCE TO RELATED APPLICATIONS

This application is a continuation of U.S. application Ser. No. 15/970,911, filed on May 4, 2018, which claims priority of Chinese Application No. 201710308089.1 filed on May 4, 2017, the entire contents of each of which are hereby incorporated by reference.

TECHNICAL FIELD

The present disclosure generally relates to the field of imaging technology, and more particularly, to a system and method for efficient scanning and image reconstruction in positron emission tomography (PET).

BACKGROUND

Positron emission tomography (PET) is a nuclear medicine functional imaging technique that is used to observe metabolic processes in a body. Specifically, in PET studies, a biologically active molecule carrying a radioactive tracer is first introduced into a patient's body. The imaging system then detects gamma rays (also referred to as PET data) emitted by the tracer and constructs a three-dimensional image of the tracer concentration within the body by analyzing the detected signals. Because the biologically active molecules used in PET studies are natural substrates of metabolism at a target organ or tissue, PET can aid the evaluation of the physiology (functionality) and/or anatomy (structure) of the target organ or tissue, as well as its biochemical properties. Changes in these properties of the target organ or tissue may provide information for the identification of the onset of a disease process before any anatomical changes relating to the disease become detectable by other diagnostic tests, such as computed tomography (CT) or magnetic resonance imaging (MRI).

PET data may be used as the basis for PET imaging and subsequent diagnostic analysis. A data collection mode of an imaging system may have a variety of ways of operation. Merely by way of example, typical data collection modes of an imaging system may include a static mode (also referred to as an emission mode), a gating mode, or a transmission mode. Generally, the static mode may be used for scanning a whole volume of a subject (e.g., the whole body of a patient) during a PET scan. When the PET tracer achieves stability in the body of the patient, the imaging system may begin to collect PET data. In order to achieve sufficient PET data for image reconstruction, the acquisition time may be relatively long under the static mode. Additionally, PET data collected from body parts that contain physiological motion may be inaccurate under the static mode. On this basis, the gating mode may be introduced. By synchronizing PET data collection with an organ motion cycle, the gating mode may reduce or eliminate the blurring effects of the organ motion. The transmission mode may be used for attenuation correction, and a transmissive scan with the corresponding emission scan may be a pair of pairing scans. Under the transmission mode, gamma rays detected by the imaging system are not emitted from the patient body, but emitted by an emission source and passed through the patient.

In order to obtain a patient's whole body PET image, the patient may generally first undergo a static scan on the patient's whole body, and the corresponding PET data may be collected in the static mode, and body parts that contain physiological motion may then undergo a gating scan to reduce or eliminate the blurring effects causing by the physiological motion. The foregoing method of obtaining a patient's whole body PET image may take too much time to scan and perform image reconstruction, and the patient experience may be poor. Therefore, it is desirable to propose an imaging system and method that may realize efficient scanning and image reconstruction in Positron Emission Tomography (PET).

SUMMARY

According to an aspect of the present disclosure, a method for determining a PET image of the scan volume based on one or more PET sub-images is provided. The method may be implemented on at least one machine each of which has at least one processor and storage. The method may include determining a scan volume of a subject supported by a scan table; dividing the scan volume into one or more scan regions; for each scan region of the one or more scan regions, determining whether there is a physiological motion in the scan region; generating, based on a result of the determination, a PET sub-image of the scan region based on first PET data of the scan region acquired in a first mode or based, at least in part, on second PET data of the scan region acquired in a second mode; and generating a PET image of the scan volume based on one or more PET sub-images.

In some embodiments, the generating a PET sub-image of the scan region based on first PET data of the scan region acquired in the first mode or based, at least in part, on second PET data of the scan region acquired in a second mode may comprise: determining that there is no physiological motion in the scan region; and in response to a determination that there is no physiological motion in the scan region, generating a PET sub-image of the scan region based on first PET data of the scan region acquired in the first mode.

In some embodiments, the generating a PET sub-image of the scan region based on first PET data of the scan region acquired in the first mode or based, at least in part, on second PET data of the scan region acquired in the second mode may comprise determining that there is the physiological motion in the scan region; and in response to a determination that there is the physiological motion in the scan region, generating the PET sub-image of the scan region based, at least in part, on second PET data of the scan region acquired in the second mode.

In some embodiments, the first mode may be a static mode, and the second mode may be a gating mode.

In some embodiments, for each scan region of the one or more scan regions, the determining whether there is a physiological motion in the scan region may comprise obtaining reference PET data of the scan region acquired in the first mode or in the second mode; dividing the reference PET data of the scan region into a plurality of data frames; obtaining a motion curve based on the plurality of data frames; and determining whether there is the physiological motion in the scan region based on the motion curve.

In some embodiments, the reference PET data may be at least part of the first PET data of the scan region acquired in the first mode.

In some embodiments, for each scan region of the one or more scan regions, the determining whether there is a physiological motion in the scan region based on the motion curve may comprise obtaining a spectrum characteristic corresponding to the motion curve; and obtaining a physiological motion characteristic based on the spectrum characteristic.

In some embodiments, each scan region of the one or more scan regions corresponds to a position of the scan table, and the method may comprises assigning different marks corresponding to each scan region of the one or more scan regions; generating first information relating to each scan region of the one or more scan regions based on the different marks; for each scan region of the one or more scan regions, the determining whether there is a physiological motion in the scan region comprising determining whether there is a physiological motion in the scan region based on the first information.

In some embodiments, the method may further comprise obtaining a topogram of the one or more scan regions of the scan volume, wherein for each scan region of the one or more scan regions, the determining whether there is a physiological motion in the scan region comprises determining whether there is a physiological motion in the scan region based on the topogram.

In some embodiments, the PET image of the scan volume is generated by stitching the one or more PET sub-images of the one or more scan regions.

According to an aspect of the present disclosure, a system for determining a PET image of the scan volume based on one or more PET sub-images is provided. The system may include a computer-readable storage medium storing executable instructions and at least one processor in communication with the computer-readable storage medium. When the executable instructions are executed, the executable instructions may cause the system to implement a method. The method may include determining a scan volume of a subject supported by a scan table; dividing the scan volume into one or more scan regions; for each scan region of the one or more scan regions, determining whether there is a physiological motion in the scan region; generating, based on a result of the determination, a PET sub-image of the scan region based on first PET data of the scan region acquired in a first mode or based, at least in part, on second PET data of the scan region acquired in a second mode; and generating a PET image of the scan volume based on one or more PET sub-images.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include determining a scan volume of a subject supported by a scan table; dividing the scan volume into one or more scan regions; for each scan region of the one or more scan regions, determining whether there is a physiological motion in the scan region; generating, based on a result of the determination, a PET sub-image of the scan region based on first PET data of the scan region acquired in a first mode or based, at least in part, on second PET data of the scan region acquired in a second mode; and generating a PET image of the scan volume based on one or more PET sub-images.

According to another aspect of the present disclosure, a system for determining a PET image of the scan volume based on one or more PET sub-images is provided. The system may comprise a division unit configured to divide a scan volume of a subject into one or more scan regions; a determination unit configured to, for each scan region of the one or more scan regions, determine whether there is physiological motion in the scan region; and a reconstruction unit configured to generate, based on a result of the determination, a PET sub-image of the scan region based on first PET data of the scan region acquired in a first mode or based, at least in part, on second PET data of the scan region acquired in a second mode; and a stitching unit configured to generate a PET image of the scan volume based on one or more PET sub-images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
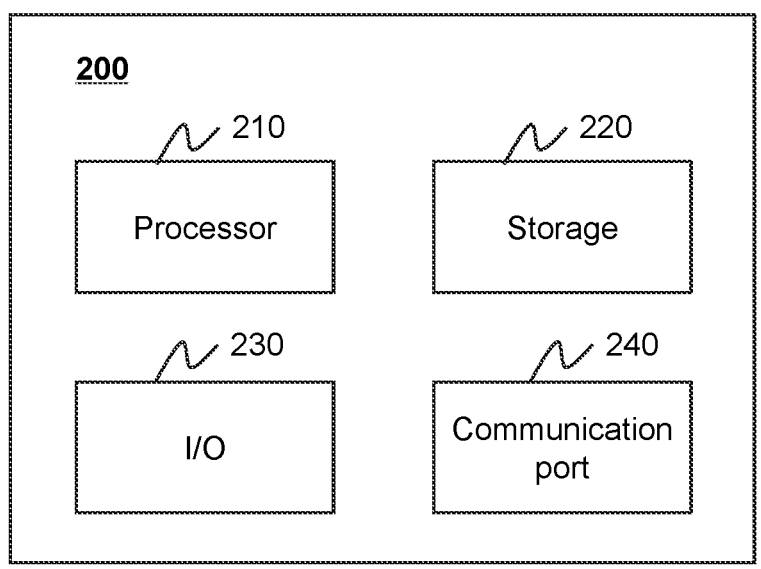
FIG. 2 is a schematic diagram illustrating an exemplary computing device on which the imaging system can be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are PET systems and methods for non-invasive imaging, such as for disease diagnostic and/or research purposes. The imaging system may find its applications in different fields such as medicine or industry. For example, the imaging system may be used in internal inspection of components including, for example, flaw detection, security scanning, failure analysis, metrology, assembly analysis, void detection, wall thickness assessment, or the like, or any combination thereof. The present disclosure provide systems and methods for PET image reconstruction. A predetermined scan region is divided into one or more sub scan regions, and each of the sub scan region corresponds to a position of a scan table. Then whether a physiological motion exists in a position of a scan table is determined. If there is no physiological motion, PET data related to the sub scan region may be obtained by static mode. If there is a physiological motion, PET data related to the sub scan region may be obtained by gating mode. Thus, the whole scanning and image reconstruction time may be reduced.

The following description is provided to help better understanding PET image reconstruction methods and/or systems. The term "image" used in this disclosure may refer to a 2D image, a 3D image, a 4D image, and/or any related image data (e.g., PET data, projection data corresponding to the PET data). The image data may correspond to a distribution of PET tracer molecules within the subject (e.g., a patient) or a coincidence distribution of a plurality of voxels within the subject represented in the sonogram. As used herein, the PET tracer may refer to a substance that may undergo certain changes under the influence of an activity or functionality within the subject, whose activity and/or functionality are to be visualized and/or studied.

For illustration purposes, the following description is provided to help better understanding a PET imaging system. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
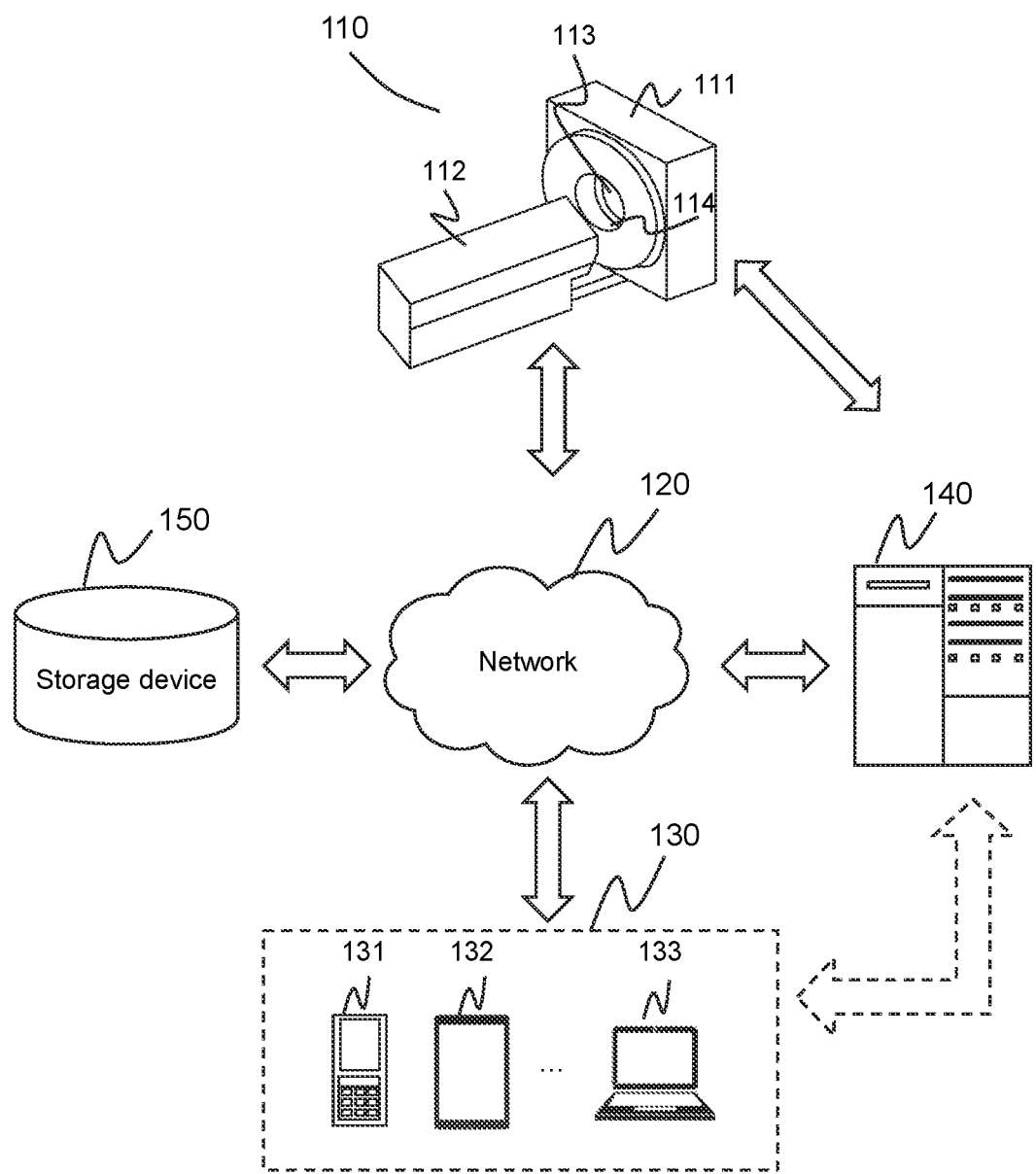
FIG. 1 is a schematic diagram illustrating an exemplary PET system according to some embodiments of the present disclosure.

FIG. 1 is a schematic diagram illustrating an exemplary imaging system 100 according to some embodiments of the present disclosure. Imaging system 100 may be a single-modality system. Exemplary single-modality system may include a single-photon emission computed tomography (SPECT) system, a positron emission computed tomography system, etc. Imaging system 100 may also be a multi-modality system. Exemplary multi-modality systems may include a computed tomography-positron emission tomography (CT-PET) system, a magnetic resonance-positron emission tomography (MR-PET) system, etc. In some embodiments, the multi-modality imaging system may include modules and/or components for performing emission computed tomography imaging and/or related analysis.

For illustration purposes, as shown in FIG. 1, imaging system 100 may include PET scanner 110, network 120, one or more terminals 130, processing device 140, and storage device 150. The components in imaging system 100 may be connected in one or more of various ways. Merely by way of example, PET scanner 110 may be connected to processing device 140 through network 120. As another example, PET scanner 110 may be connected to processing device 140 directly. As a further example, one or more terminals 130 may be connected to another component of imaging system 100 (e.g., processing device 140) via network 120 as illustrated in FIG. 1. As still a further example, at least one terminal 130 may be connected to processing device 140 directly as illustrated by the dotted arrow in FIG. 1. As still a further example, storage device 150 may be connected to another component of imaging system 100 (e.g., processing device 140) directly as illustrated in FIG. 1, or through network 120.

PET scanner 110 may include a gantry 111, a scan table 112, a detection region 113, and a detector 114. PET scanner 110 may scan a subject and obtain information related with the subject. Gantry 111 may support the components necessary to produce and detect radiation events to generate an image. Scan table 112 may position a subject in detection region 113. Detector 114 may detect radiation events (e.g., gamma photons) emitted from detection region 113. In some embodiments, detector 114 may include a plurality of detector units. The detector units may be implemented in a suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT.

In some embodiments, the detected radiation events may be stored or archived in a storage (e.g., storage device 150), displayed on a display (e.g., a screen on a computing device), or transferred to a connected device (e.g., an external database). In some embodiments, a user may control PET scanner 110 via a computing device.

In some embodiments, a CT scanner may be added to imaging system 100, and imaging system 100 may be a multi-modality imaging system. For example, PET scanner 110 and the CT scanner may be installed separately on a gantry so that PET scanner 110 does not interfere with the operation of the CT scanner. The CT scanner may be a spiral CT, an electron beam CT, an energy spectrum CT, etc. In some embodiments, the spiral CT may be a multi-slice spiral CT or a multi-row spiral CT.

In some embodiments, a camera may be added to imaging system 100, e.g., the camera may be installed on gantry 111. In general, the camera may include imaging elements, imaging media, and an imaging control structure. The imaging elements may be a lens group made of optical glass, called a lens. The imaging media may be used for capturing and recording images. Exemplary imaging media may include film, charge coupled device (CCD), complementary metal-oxide-semiconductor transistor (CMOS), etc. The darkroom may provide a connection between the lens and the imaging media, and protect the imaging media from interference. The imaging control structure may change the way of imaging or recording images. Exemplary imaging control structures may include an aperture, a shutter, a focus control, etc.

In some embodiments, the camera may identify different marks of scan table 112 through various image identification techniques. A mark may include a serial number, a quick response code (QR code), a barcode, or the like, or any combination thereof. In some embodiments, such a mark may provide position information of the scan table or the scan region. For instance, the PET scanner 110 may determine the position information in the scan region based on the position of the scan table and an identified mark. Exemplary image identification techniques may include a neural network based image identification technique, a wavelet moment based image identification technique, a fractal feature-based image identification technique, etc. In some embodiments, the camera may identify a position of the scan table.

In some embodiments, the PET scan may be implemented by scanning one or more scan regions of a scan volume of a subject. The one or more scan regions may be generated by dividing the scan volume of the subject into one or more parts. In some embodiments, the scan volume of the subject may be the entire volume of the subject. In some embodiments, the scan volume of the subject may be a portion of the subject. A scan region may correspond to a portion of a scan table on which the subject is placed during the PET scan. By moving scan table 112 into detection region 113 along the z-axis, each of the one or more scan regions may be scanned. PET data of respective scan regions may then be obtained. At least two scan regions of the one or more scan regions may at least partially overlap. In some embodiments, the one or more scan regions may completely cover the scan volume of the subject. A PET sub-image may be generated based on PET data of a scan region. The PET image of the scan volume of the subject may be obtained by stitching one or more PET sub-images of the one or more scan regions. The PET image of the scan volume of the subject may also be directly obtained based on the entire PET data of the one or more scan regions.

Network 120 may include any suitable network that can facilitate the exchange of information and/or data for imaging system 100. In some embodiments, one or more components of imaging system 100 (e.g., PET scanner 110, terminal 130, processing device 140, storage device 150, etc.) may communicate information and/or data with one or more other components of imaging system 100 via network 120. For example, processing device 140 may obtain image data from PET scanner 110 via network 120. As another example, processing device 140 may obtain user instructions from terminal 130 via network 120. Network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, network 120 may include one or more network access points. For example, network 120 may include wired and/or wireless network access points such as base stations and/or internet exchange points through which one or more components of imaging system 100 may be connected to network 120 to exchange data and/or information.

Figure 3:
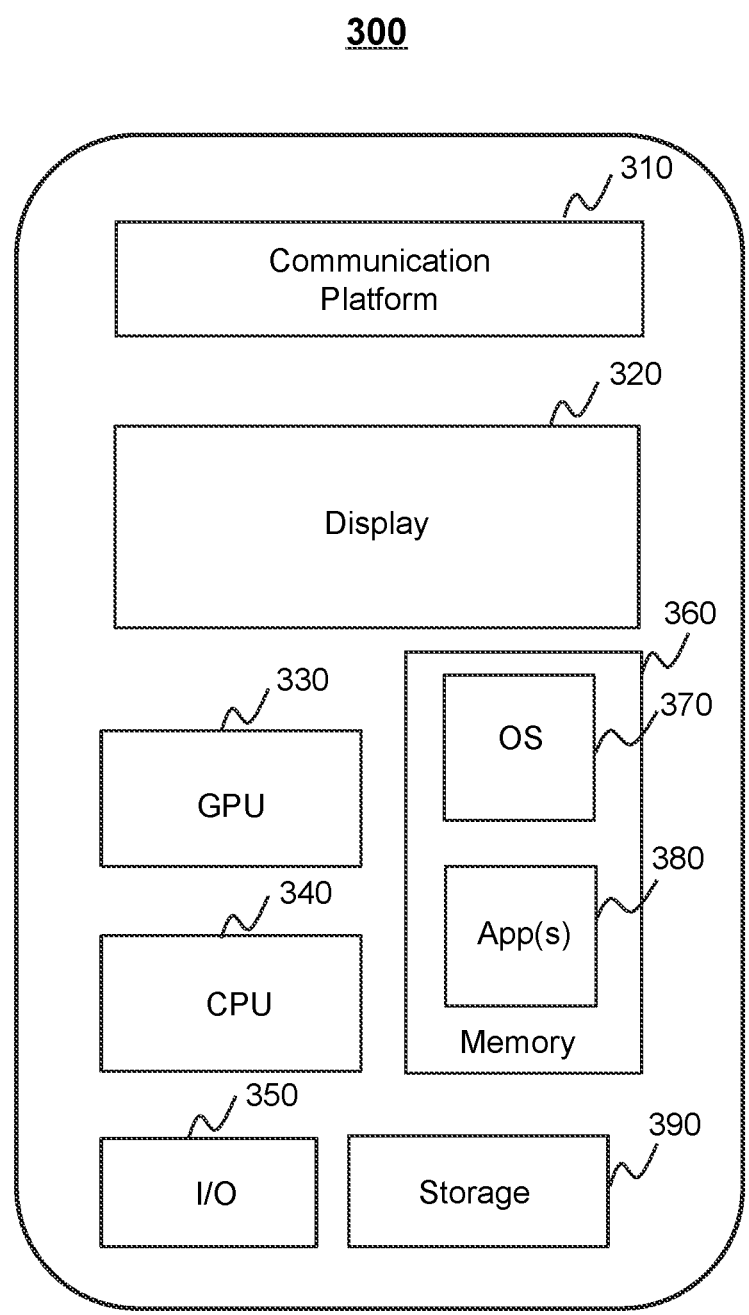
FIG. 3 is a schematic diagram illustrating hardware and/or software components of an exemplary mobile device according to some embodiments of the present disclosure.

Terminal(s) 130 may include a mobile device 131, a tablet computer 132, a laptop computer 133, or the like, or any combination thereof. In some embodiments, mobile device 131 may include a smart home device, a wearable device, a mobile device, a virtual reality device, an augmented reality device, or the like, or any combination thereof. Merely by way of example, terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, terminal(s) 130 may be part of processing device 140.

Processing device 140 may process data and/or information obtained from PET scanner 110, terminal(s) 130, and/or storage device 150. In some embodiments, processing device 140 may be a single server or a server group. The server group may be centralized or distributed. In some embodiments, processing device 140 may be local or remote. For example, processing device 140 may access information and/or data stored in PET scanner 110, terminal(s) 130, and/or storage device 150 via network 120. As another example, processing device 140 may be directly connected to PET scanner 110, terminal(s) 130 and/or storage device 150 to access stored information and/or data. In some embodiments, processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, processing device 140 may be implemented by a computing device 200 having one or more components as illustrated in FIG. 2.

Storage device 150 may store data, instructions, and/or any other information. In some embodiments, storage device 150 may store data obtained from terminal(s) 130 and/or processing device 140. In some embodiments, storage device 150 may store data and/or instructions that processing device 140 may execute or use to perform exemplary methods described in the present disclosure. In some embodiments, storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, storage device 150 may be connected to network 120 to communicate with one or more other components of imaging system 100 (e.g., processing device 140, terminal(s) 130). One or more components of imaging system 100 may access the data or instructions stored in storage device 150 via network 120. In some embodiments, storage device 150 may be directly connected to or communicate with one or more other components of imaging system 100 (e.g., processing device 140, terminal(s) 130). In some embodiments, storage device 150 may be part of processing device 140.

FIG. 2 is a schematic diagram illustrating an exemplary computing device on which an imaging system can be implemented, according to some embodiments of the present disclosure. As illustrated in FIG. 2, computing device 200 may include processor 210, storage 220, input/output (I/O) 230, and communication port 240.

Computing device 200 may be a general purpose computer or a special purpose computer. Both may be used to implement imaging system 100 of the present disclosure. Computing device 200 may be used to implement any component of the service as described herein. For example, processing device 140 of imaging system 100 may be implemented on computing device 200, via its hardware, software program, firmware, or a combination thereof. Although only one such computer is shown for convenience, the computer functions related to the imaging system as described herein may be implemented in a distributed manner on a number of similar platforms to distribute the processing load.

Processor 210 may execute computer instructions (program code) and perform functions of processing module 440 in accordance with techniques described herein. Computer instructions may include routines, programs, objects, components, data structures, procedures, modules, and functions, which perform particular functions described herein. For example, processor 210 may process the data or information received from control module 410, acquisition module 420, storage module 430, or any other component of imaging system 100. In some embodiments, processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, processor 210 may include a microcontroller to process PET data from PET scanner 110 for image reconstruction.

Storage 220 may store the data or information received from control module 410, acquisition module 420, storage module 430, processing module 440, or any other component of imaging system 100. In some embodiments, storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, storage 220 may store one or more programs and/or instructions to perform exemplary methods described in the present disclosure. For example, storage 220 may store a program for processing module 440 for reconstructing a PET image based on PET data.

Input/output (I/O) 230 may input and/or output signals, data, information, etc. In some embodiments, input/output (I/O) 230 may enable user interaction with processing device 140. In some embodiments, input/output (I/O) 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

Communication port 240 may be connected to a network (e.g., network 120) to facilitate data communications. Communication port 240 may establish connections between PET scanner 110 and processing device 140, storage device 150, and/or one or more terminals 130. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, communication port 240 may be and/or include a standardized communication port, such as RS232, RS485, etc. In some embodiments, communication port 240 may be a specially designed communication port. For example, communication port 240 may be designed in accordance with the digital imaging and communications in medicine (DICOM) protocol.

Merely for illustration, only one CPU and/or processor is illustrated in computing device 200. However, it should be noted that computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the processor of computing device 200 executes both operations A and operation B, it should be understood that operation A and operation B may also be performed by two or more different processors jointly or separately in computing device 200 (e.g., a first processor executes operation A and a second processor executes operation B, or the first and second processors jointly execute operations A and B).

FIG. 3 is a schematic diagram illustrating exemplary hardware and/or software components of an exemplary mobile device on which terminal(s) 130 may be implemented according to some embodiments of the present disclosure. As illustrated in FIG. 3, mobile device 300 may include communication platform 310, display 320, graphics processing unit (GPU) 330, central processing unit (CPU) 340, I/O 350, memory 360, and storage 390. In some embodiments, any other suitable component, including but not limited to a system bus or a controller (not shown), may also be included in mobile device 300. In some embodiments, mobile operating system 370 (e.g., iOS™, Android™, Windows Phone™) and one or more applications 380 may be loaded into memory 360 from storage 390 in order to be executed by CPU 340. Applications 380 may include a browser or any other suitable mobile apps for receiving and rendering information relating to image processing or other information from processing device 140. User interactions with the information stream may be achieved via I/O 350 and provided to processing device 140 and/or other components of imaging system 100 via network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
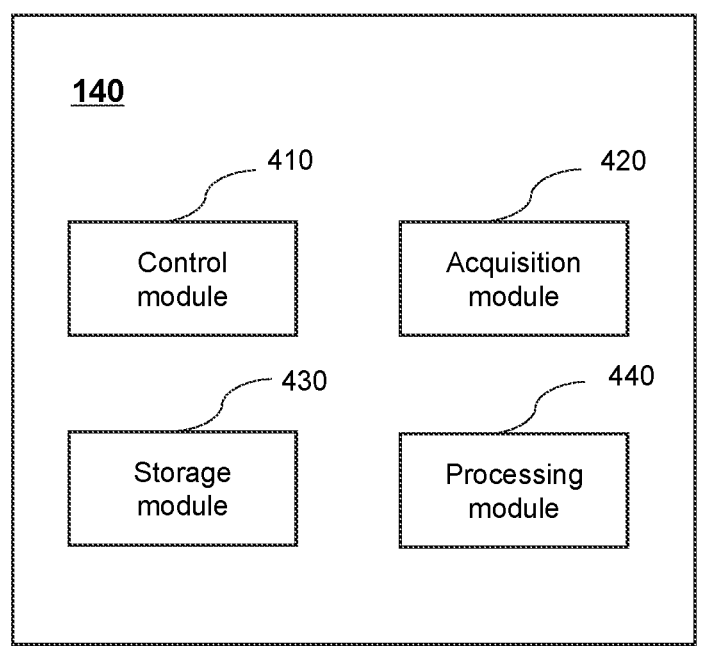
FIG. 4 is a block diagram illustrating an exemplary processing device according to some embodiments of the present disclosure.

FIG. 4 is a block diagram illustrating an exemplary processing device according to some embodiments of the present disclosure. Processing device 140 may include a control module 410, acquisition module 420, storage module 430, and processing module 440. Processing device 140 may be implemented on various components (e.g., computing device 200 as illustrated in FIG. 2, mobile device 300 as illustrated in FIG. 3).

Control module 410 may generate a control parameter for controlling acquisition module 420, storage module 430, and/or processing module 440. For example, control module 410 may control acquisition module 420 as to whether to acquire PET data, or the time when PET data acquisition may occur, or collection mode that PET data acquisition may use. As another example, control module 410 may control processing module 440 to select different algorithms to process PET dataset acquired by acquisition module 420. In some embodiments, control module 410 may receive a real-time or a predetermined command provided by a user (e.g., a doctor) and adjust acquisition module 420, and/or processing module 440 to take images of a subject according to the received command. In some embodiments, control module 410 may communicate with other modules in imaging system 100 for exchanging information or data.

Acquisition module 420 may acquire or receive information/data. Merely by way of example with reference to a PET imaging system, acquisition module 420 may acquire or receive PET data. In some embodiments, during a PET scan or analysis, PET tracer (also referred to as "PET tracer molecules") is first introduced into the subject before an imaging process begins. During the PET scan, the PET tracer molecules may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation may result in two photons, e.g., 511 keV gamma photons, which, upon their own generation, begin to travel in opposite directions with respect to one another. The line connecting the two photons may be referred to as a line of response (LOR). Acquisition module 420 may obtain the trajectory and/or information of the photons (also referred to as the "PET data"). For example, the PET data may include a list of annihilation events, transverse and longitudinal positions of the LORs, or the like, or a combination thereof. In some embodiments, the PET data may be used to determine the distribution of the PET tracer molecules in the image domain and/or the coincidence distribution of voxels in the sinogram coordinate system.

In some embodiments, the PET tracer may include carbon (11C), nitrogen (13N), oxygen (15O), fluorine (18F), or the like, or a combination thereof. In some embodiments, for a SPECT system, a SPECT tracer may be introduced into the subject. The SPECT tracer may include technetium-99m, iodine-123, indium-111, iodine-131, or the like, or a combination thereof. Accordingly, in some embodiments, the PET tracer or SPECT tracer of the present disclosure may be organic compounds containing one or more of such isotopes. These tracers are either similar to naturally occurring substances or otherwise capable of interacting with the functionality or activity of interest within the subject. Hence, distributional information of the tracer may be used as an indicator of the subject functionality.

In some embodiments, acquisition module 420 may, for a scan region, acquire first PET data of the scan region in a first mode when, e.g., there is no physiological motion in the scan region. The first mode may include the static mode, the transmission mode, or the like, or any combination thereof. In some embodiments, acquisition module 420 may acquire second PET data of the scan region in a second mode when, e.g., there is physiological motion in the scan region. The second mode may include the gating mode, etc.

Storage module 430 may store information. The information may include image data from acquisition module 420, operation instructions of a user obtained via, e.g., communication port 240, results generated by processing module 440, etc. Storage module 430 may store information in the form of text, a digital document, sound, an image, a video, etc. In some embodiments, storage module 430 may be a storage device of one of various types such as a solid-state hard disk, a mechanical hard disk, a universal serial bus (USB) flash memory, a secure digital (SD) memory card, an optical disk, a random-access memory (RAM), a read-only memory (ROM), etc. In some embodiments, storage module 430 may be one or more mass storages, for example, a mass storage array managed by one or more controllers. In some embodiments, storage module 430 may be a local storage device of processing device 140, an external storage device, a distributed storage device (e.g., cloud storage, etc.) that is communicatively connected via network 120, etc.

Processing module 440 may process information/data provided by various modules in imaging system 100. Processing module 440 may process image data acquired by acquisition module 420 or retrieved from storage module 430, etc. In some embodiments, processing module 440 may determine whether there is physiological motion in a scan region based on the image data corresponding to the scan region, reconstruct an image based on the image data according to a reconstruction algorithm, and/or perform any other functions for image stitching in accordance with various embodiments of the present disclosure. Exemplary reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, processing module 440 may be one or more processing components or devices, such as a central processing unit (CPU), a graphics processing unit (GPU), a digital signal processor (DSP), a system on a chip (SoC), a microcontroller unit (MCU), etc. In some embodiments, processing module 440 may also be a specially designed processing component or device with special functions.

It should be noted that the above descriptions of processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, processing device 140 may include one or more other modules. However, those variations and modifications also fall within the scope of the present disclosure.

Figure 5:
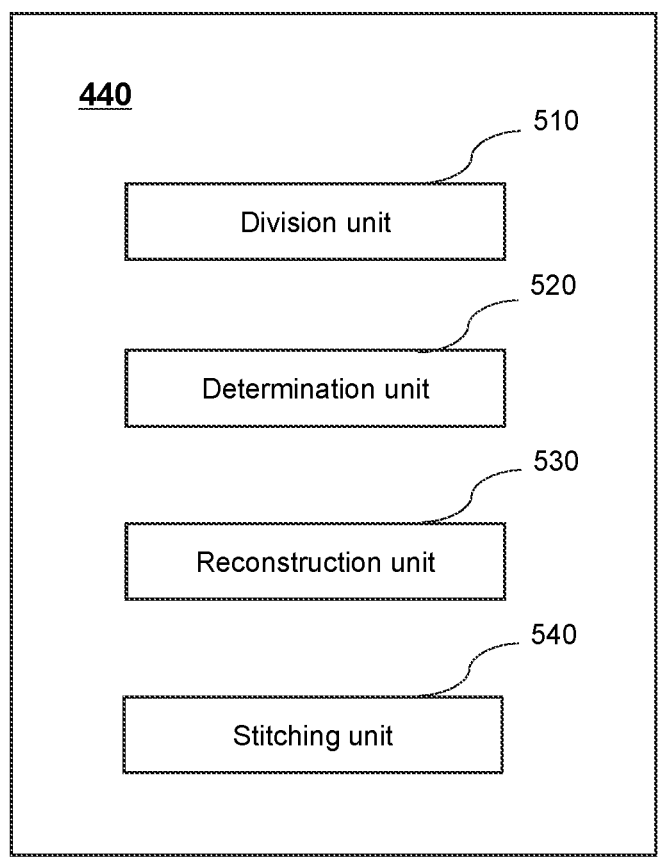
FIG. 5 is a block diagram illustrating an exemplary processing module according to some embodiments of the present disclosure.

FIG. 5 is a block diagram illustrating an exemplary processing module according to some embodiments of the present disclosure. Processing module 440 may include division unit 510, determination unit 520, reconstruction unit 530, and stitching unit 540. In some embodiments, the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof).

Division unit 510 may divide a scan volume of a subject into one or more scan regions. The one or more scan regions may be superimposed, and the superimposed scan region may completely cover the scan volume of the subject. Each scan region of the one or more scan regions may correspond to a table position. By moving scan table 112 into the detection region 113, each scan region may be scanned. PET data of the respective scan regions may then be obtained by PET detectors. A PET image of the scan volume of the subject may be obtained by stitching one or more PET sub-images of the one or more scan regions, wherein the one or more PET sub-images may be generated based on corresponding PET data of the respective scan regions.

Merely by way of example, when the subject is a patient, the scan volume of the patient may be divided into three scan regions corresponding to head, chest and abdomen, and the lower body. In some embodiments, the scan volume of the patient may be evenly divided into one or more scan regions according to a size of a scan region. The size of a scan region may be set by a doctor in advance, or may be set based on the patient's height, or may be set based on a size structure of a PET scanner, or the like. In some embodiments, the PET image of the subject may also be directly obtained based on entire PET data of the one or more scan regions.

Determination unit 520 may, for each scan region of the one or more scan regions, determine whether there is physiological motion in the scan region. In some embodiments, after completing a determination on a scan region, determination unit 520 may generate a determined signal (e.g., 0, 1, etc.) and transmit the determined signal to acquisition module 420. Acquisition module 420 may then select a mode for PET data collection. For example, in response to a determination performed by determination unit 520 that there is no physiological motion in the scan region, a determined signal 1 may be generated and transmitted to acquisition module 420. Acquisition module 420 may then, for the scan region, perform data collection in a first mode. The first mode may include the static mode, the transmission mode, or the like, or any combination thereof. As another example, in response to a determination performed by determination unit 520 that there is physiological motion (e.g., respiration, heartbeat, etc.) in the scan region, a determined signal 0 may be generated and transmitted to acquisition module 420. Acquisition module 420 may then, for the scan region, perform data collection in a second mode. The second mode may include the gating mode, etc.

The determination whether there is physiological motion in a scan region of the one or more scan regions may be implemented in various ways by determination unit 520. In some embodiments, data collection may be first performed in the first mode for the subject so that determination unit 520 may determine whether there is physiological motion in a scan region based on first PET data of the scan region acquired in the first mode. In such embodiments, acquisition module 420 may then, for a scan region, perform further data collection in the second mode only after determination unit 520 determines there is physiological motion in the scan region; while for a scan region where determination unit 520 determines that there is no physiological motion, no further data acquisition is needed. In some embodiments, the amount of data from the data acquired in the first mode used for determining whether there is physiological motion and the amount of data from the data acquired in the first mode used for image reconstruction for, e.g., diagnosis, display, etc., may be different. For instance, a smaller amount of data from the data acquired in the first mode is used for determining whether there is physiological motion than for image reconstruction for, e.g., diagnosis, display, etc. In some embodiments, a quick and/or coarse data collection may be first performed in the first mode for the subject on the basis of which determination unit 520 may determine whether there is physiological motion in a scan region. On the basis of the determination, a normal data acquisition may be performed in the first mode or the second mode, and images of desired quality may be generated based on the data acquired this way. In some embodiments, determination unit 520 may determine whether there is physiological motion in a scan region based on a topogram of the subject. The topogram may be a CT topogram obtained by the CT scanner. In some embodiments, the topogram may be obtained by a camera. In some embodiments, determination unit 520 may determine whether there is physiological motion in a scan region based on different marks of scan table 112. In some embodiments, determination unit 520 may determine whether there is physiological motion in a scan region based on the position of the scan table 112. In some embodiments, determination unit 520 may determine whether there is physiological motion in a scan region by an external device, such as a vital signs monitor, etc. An exemplary vital signs monitor may include a bandage set on the patient, an electrocardiograph (ECG) device, a respiratory monitor, etc.

Reconstruction unit 530 may reconstruct an image. In some embodiments, reconstruction unit 530 may include a microprocessor, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or a combination thereof.

In some embodiments, reconstruction unit 530 may reconstruct a PET sub-image of the one or more scan regions, respectively. Reconstruction unit 530 may employ different kinds of imaging reconstruction techniques for the image reconstruction procedure. In some embodiments, reconstruction unit 530 may reconstruct a PET sub-image based on second PET data of the scan region acquired by acquisition module 420 in the second mode, when there is physiological motion in the scan region. Exemplary reconstruction techniques may include vital signs monitor (VSM) gating reconstruction, digital gating reconstruction, etc. In some embodiments, reconstruction unit 530 may reconstruct a PET sub-image based on first PET data of the scan region acquired by acquisition module 420 in the first mode, when there is no physiological motion in the scan region. Exemplary reconstruction techniques may include static image reconstruction, etc.

In some embodiments, reconstruction unit 530 may further adjust statistical characteristics of the one or more scan regions corresponding to different table positions to keep consistent, and ensuring quantitative correctness thereof. The statistical characteristics may include scan time period of a scan region corresponding to a table position, scan velocity of a scan region corresponding to a table position, the number of data frames of a scan region corresponding to a table position, or the like, or any combination thereof.

Stitching unit 540 may obtain a PET image of the scan volume by stitching PET sub-images of the one or more scan regions. Stitching unit 540 may employ different kinds of imaging stitching techniques for stitching the PET sub-images. Exemplary image stitching techniques may include a frequency domain based technique (phase correlation technique), or a time domain based technique, or the like. In some embodiments, stitching unit 540 may use different image stitching algorithms including a Fourier phase correlation algorithm, a point-registration algorithm, an intensity based algorithm, etc.

In some embodiments, stitching unit 540 may include, before the stitching procedure, adjusting a weight ratio and smoothing coefficient of an overlapped part formed by a static reconstructed PET sub-image and a gating reconstructed PET sub-image. Image quality of the overlapped part during the stitching procedure may be improved.

In some embodiments, stitching unit 540 may be omitted. The PET image of the scan volume may be obtained by reconstruction unit 530. Reconstruction unit 530 may directly reconstruct the PET image of the scan volume based on PET data of all of the one or more scan regions using different reconstruction algorithms. Exemplary reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, reconstruction unit 530 may also include performing data reorganization on the PET data of all of the one or more scan regions.

It should be noted that the above descriptions of processing module 440 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, processing module 440 may include one or more other units. However, those variations and modifications also fall within the scope of the present disclosure.

Figure 6:
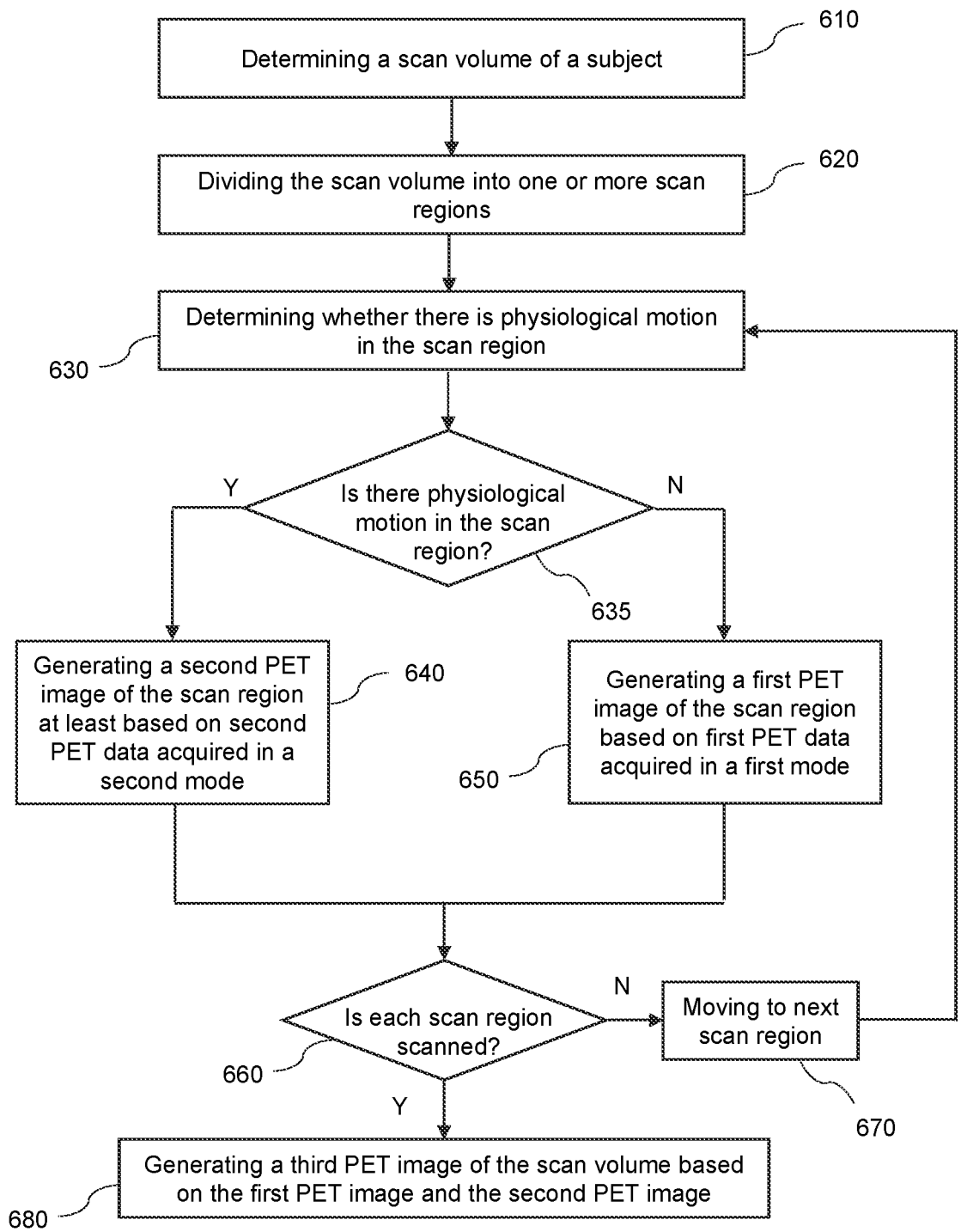
FIG. 6 is a flowchart illustrating an exemplary process for generating a PET image of the scan volume according to some embodiments of the present disclosure.

FIG. 6 is a flowchart illustrating an exemplary process for generating a PET image of a scan volume according to some embodiments of the present disclosure. Process 600, or a portion thereof, may be implemented on a computing device as illustrated in FIG. 2 or a mobile device illustrated in FIG. 3. For illustration purposes, the following description is provide with reference to the imaging system 100 as illustrated in FIG. 1.

In 610, a scan volume of a subject may be determined. In some embodiments, the scan volume of the subject may be retrieved from the storage 220. In some embodiments, the scan volume of the subject may be determined by performing a CT scan on the subject. In some embodiments, the scan volume of the subject may be determined by taking a photograph of the subject.

In 620, the scan volume of the subject may be divided into one or more scan regions. In some embodiments, division unit 510 may divide the scan volume of the subject into one or more scan regions. Two adjacent scan regions of the one or more scan regions may partially overlap, and the scan regions may completely cover the scan volume of the subject. Each scan region of the one or more scan regions may correspond to a table position. By moving scan table 112 into detection region 113, each scan region may be scanned.

For instance, a scan volume of a patient may be divided into three scan regions including a head portion, a chest and abdomen portion, and a lower body portion. Each of the three scan regions may correspond to a table position. For instance, the head portion corresponds to a table position 1, the chest and abdomen portion corresponds to a table position 2, and the lower body portion corresponds to a table position 3. When the scan table 112 moving into detection region 113 reaches the table position 1, the head of the patient corresponding to the table position 1 may be scanned. When scan table 112 moving into detection region 113 reaches the table position 2, the chest and abdomen of the patient corresponding to the table position 2 may be scanned. When scan table 112 moving into detection region 113 reaches the table position 3, the legs of the patient corresponding to the table position 3 may be scanned.

It should be noted that the above descriptions of the scan region are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the scan volume of the subject may be divided into scan region(s) in various ways. In some embodiments, the one or more scan regions may be scanned in various orders. However, those variations and modifications also fall within the scope of the present disclosure.

In 630, a determination may be made as to whether there is physiological motion in a scan region of the one or more scan regions. By moving scan table 112 arriving at a table position in detection region 113, a scan region corresponding to the table position may be moved into detection region 113. Merely by way of examples, when the subject is a patient, determination unit 520 may then determine whether there is physiological motion in the scan region of the patient. In some embodiments, determination unit 520 may determine whether there is physiological motion in the scan region of the patient based on a topogram of the patient. The topogram of the patient may be obtained through a low dose scan by a CT scanner in advance. The topogram may be presented in different grayscales, which reflect the degree of X-ray absorption by human organs and tissues. In the topogram, dark shadows may indicate low absorption areas, i.e., low-density areas such as lungs. White shadows may indicate high absorption areas, i.e., high-density areas such as bones. Under this situation, the topogram of the patient may locate organs and/or tissues in the patient's scan volume.

After analyzing the topogram of the patient, for example, when a scan region includes the lungs or part of the lungs, determination unit 520 may determine that there is respiration motion in the scan region of the patient. As another example, when a scan region includes the heart or part of the heart, determination unit 520 may determine that there is cardiac motion in the scan region of the patient. As still another example, when a scan region only includes legs or part of legs, determination unit 520 may determine that there is no physiological motion in the scan region of the patient.

In some embodiments, determination unit 520 may determine whether there is physiological motion in the scan region of the patient based on reference PET data of the scan region acquired in the first mode or in the second mode. In some embodiments, the reference PET data may be acquired before the acquisition of first PET data of the scan region in the first mode or before the acquisition of second PET data of the scan region in the second mode. In some embodiments, the reference PET data may be at least part of the first PET data of the scan region acquired in the first mode or second PET data of the scan region acquired in the second mode. Detailed descriptions may be found in FIG. 7, and descriptions thereof. In some embodiments, determination unit 520 may determine whether there is physiological motion in the scan region of the patient based on a mark on scan table 112. Detailed descriptions may be found in FIG. 10, and descriptions thereof. In some embodiments, determination unit 520 may determine whether there is physiological motion in the scan region of the patient by an external device, such as a vital signs monitor, etc. An exemplary vital signs monitor may include an electrocardiograph (ECG) device, a respiratory monitor, etc.

In 635, in response to the determination that there is physiological motion detected in the scan region, process 600 may proceed to 640. A physiological motion may include respiratory motion, cardiac motion, gastrointestinal motion, or the like, or any combination thereof. In response to the determination that there is no physiological motion in the scan region, process 600 may proceed to 650.

In 640, when there is physiological motion in the scan region, a PET sub-image of the scan region may be generated based, at least in part, on second PET data acquired in the second mode. In some embodiments, when determination unit 520 determines that there is physiological motion in the scan region, determination unit 520 may generate a determined signal (e.g., 0) and transmit the determined signal to acquisition module 420. Acquisition module 420 may obtain the second PET data of the scan region in the second mode. Reconstruction unit 530 may reconstruct a PET sub-image of the scan region based on the second PET data of the scan region. Exemplary reconstruction techniques may include a VSM reconstruction technique, a digital reconstruction technique, etc.

In some embodiments, when there is physiological motion in the scan region, the PET sub-image of the scan region may be generated based on the second PET data of the scan region acquired in the second mode and other PET data of the scan region. For example, the PET sub-image of the scan region may be generated based on the second PET data of the scan region acquired in the second mode and a first PET data of the scan region acquired in the first mode. Detailed descriptions may be found in FIG. 12, and descriptions thereof.

In 650, when there is no physiological motion detected in the scan region, a PET sub-image of the scan region may be generated based on first PET data acquired in the first mode. In some embodiments, when determination unit 520 determines that there is no physiological motion in the scan region, determination unit 520 may generate a determined signal (e.g., 1) and transmit the determined signal to acquisition module 420. Acquisition module 420 may acquire the first PET data of the scan region in the first mode. Reconstruction unit 530 may reconstruct a PET sub-image of the scan region based on the first PET data of the scan region. Exemplary reconstruction method may include a static reconstruction method, etc.

In 660, when there is a scan region left to be scanned, process 600 may proceed to 670. When each scan region of the one or more scan regions is scanned, process 600 may proceed to 680. In some embodiments, control module 410 may determine whether there is a scan region left to be scanned. For example, control module 410 may count scanned scan region(s). If the number of the scanned scan region(s) does not reach a threshold (i.e., the number of scan regions divided by division unit 510, such as 3), control module 410 may determine that there is a scan region left to be scanned. If the number of the scanned scan region(s) reaches the threshold (i.e., the number of scan regions divided by division unit 510, such as 3), control module 410 may determine that there is no scan region left to be scanned.

In 670, a next scan region may be moved into detection region 113. In some embodiments, control module 410 may move scan table 112 to next table position; next scan region may then be moved into detection region 113. Processing device 140 (e.g., processing module 440) may cause operations 630 to 660 to be repeated on the next scan region.

In 680, a PET image of the scan volume may be generated based on one or more PET sub-images. In some embodiments, reconstruction unit 530 may generate the one or more PET sub-images according to PET data of corresponding scan regions, respectively. Stitching unit 540 may generate the PET image of the scan volume by stitching the one or more PET sub-images. Exemplary image stitching techniques may include a frequency domain based technique (phase correlation technique), or a time domain based technique, or the like. In some embodiments, stitching unit 540 may use different image stitching algorithms including a Fourier phase correlation algorithm, a point-registration algorithm, an intensity-based algorithm, etc.

In some embodiments, the PET image of the scan volume may be generated by performing one-time stitching after all of the one or more PET sub-images may be obtained. In some embodiments, operation 680 may be performed before operation 660. After each of the one or more PET sub-images is obtained, an image stitching operation may be performed. Specifically, except for a first PET sub-image corresponding to a first scan region, any subsequent PET sub-image may be stitched with all PET sub-images obtained in advance. The PET image of the scan volume may be obtained until every scan region is scanned. For example, when the subject is a patient, a scan volume of the patient may be divided into three scan regions, such as a head portion, a chest and abdomen portion, and a lower body portion. A first stitched PET image may be obtained by stitching a PET sub-image of the head portion with a PET sub-image of the chest and abdomen portion. A second stitched PET image may be obtained by stitching the first stitched PET image with a PET sub-image of the legs. The second stitched PET image may be a PET image of the whole body of the patient.

In some embodiments, process 600 may include an operation for reconstruction post-processing before stitching the one or more PET sub-images. The reconstruction post-processing may include adjusting statistical characteristics of the one or more scan regions corresponding to different table positions to keep consistent, and ensuring quantitative correctness thereof. In some embodiments, reconstruction unit 530 may adjust statistical characteristics of the one or more scan regions corresponding to different table positions.

In some embodiments, process 600 may still include an operation for image stitching pre-processing before the stitching of the one or more PET sub-images. When there is an overlapped part formed by a static reconstructed PET sub-image and a gating reconstructed PET sub-image, the image stitching pre-processing may adjust a weight ratio and a smoothing coefficient of the overlapped part. In some embodiments, stitching unit 540 may, before the stitching procedure, adjust a weight ratio and a smoothing coefficient of the overlapped part.

In some embodiments, process 600 may further include an operation for setting one or more collection parameter before a collection of PET data of a scan region (e.g., before operation 640). Exemplary collection parameters may include a collection velocity, a collection time interval, a collection mode, or the like, or any combination thereof. In some embodiments, acquisition module 420 may set the collection parameter(s) based on, e.g., the number of data frames of the second mode and one or more scan parameter of the first mode. Exemplary scan parameters of the first mode may include a scanning velocity, attenuation correction, spatial resolution, a horizontal scan field, an aperture, or the like, or any combination thereof.

It should be noted that the above descriptions of process 600 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, process 600 may include one or more other operations. However, those variations and modifications also fall within the scope of the present disclosure.

Figure 7:
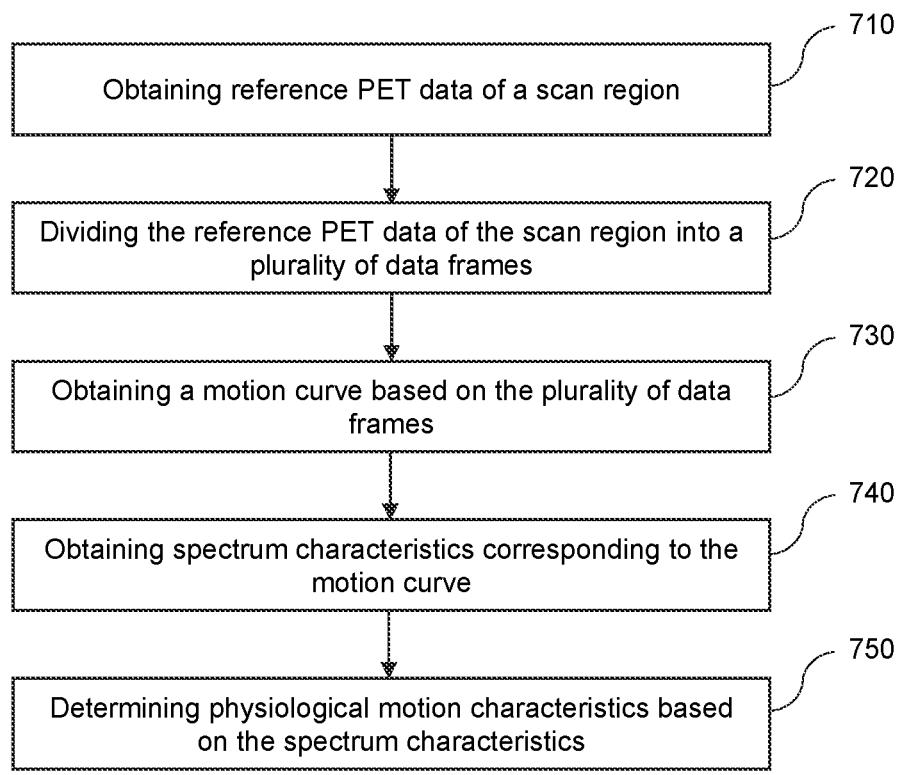
FIG. 7 is a flowchart illustrating an exemplary process for determining physiological motion characteristics of a scan region according to some embodiments of the present disclosure.

FIG. 7 is a flowchart illustrating an exemplary process for determining physiological motion characteristics of a scan region according to some embodiments of the present disclosure. Process 700, or a portion thereof, may be implemented on a computing device as illustrated in FIG. 2 or a mobile device illustrated in FIG. 3. For illustration purposes, the following description is provided with reference to process 600 as illustrated in FIG. 6. Process 700 is an exemplary process for achieving 630 of process 600.

In 710, reference PET data of a scan region in the first mode or in the second mode may be obtained. In some embodiments, acquisition module 420 may acquire the reference PET data of the scan region in the first mode. The first mode may include the static mode, the transmission mode, or the like, or any combination thereof. In some embodiments, the acquisition module 420 may acquire the reference PET data of the scan region in the second mode. The second mode may include the gating mode, etc. In some embodiments, the reference PET data of the scan region in the first mode or in the second mode may be retrieved from storage module 430.

In 720, the reference PET data of the scan region obtained in the first mode or in the second mode may be divided into a plurality of data frames. In some embodiments, determination unit 520 may divide the reference PET data of the scan region into a plurality of data frames. For example, determination unit 520 may divide the reference PET data of the scan region collected within 1.5 minutes into 900 PET data frames. Each of the 900 PET data frames may include reference PET data of the scan region collected in 100 microseconds.

Figure 8:
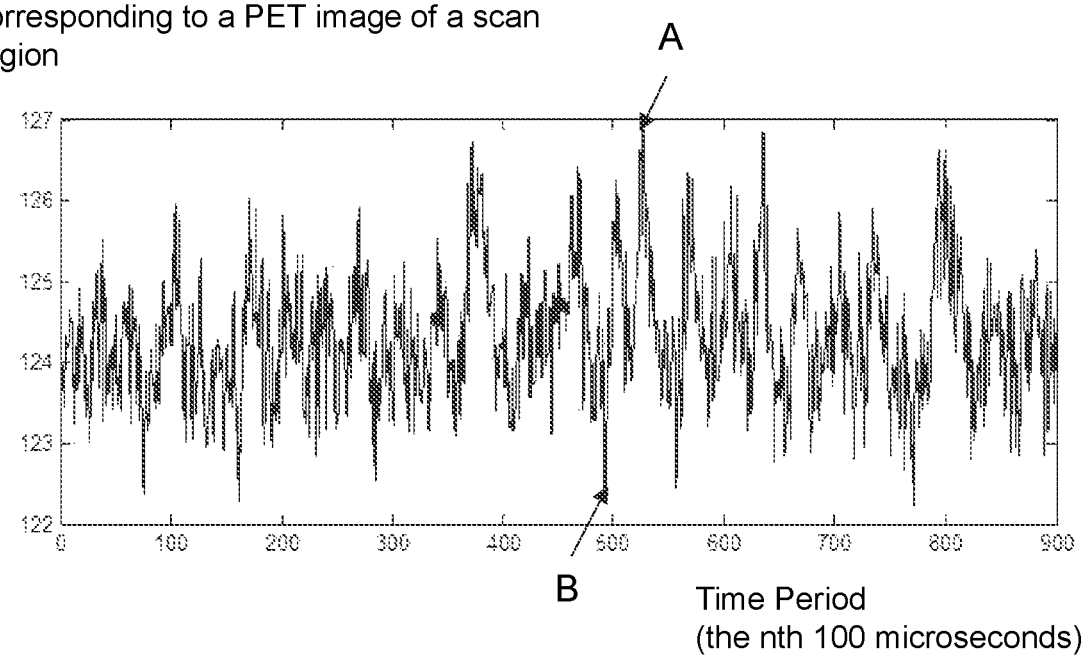
FIG. 8 is an exemplary motion curve of a scan region according to some embodiments of the present disclosure.

In 730, a motion curve may be obtained based on the plurality of data frames. In some embodiments, determination unit 520 may generate the motion curve based on the plurality of data frames. In some embodiments, the motion curve of the scan region may be obtained directly based on the plurality of data frames by performing data reorganization on the plurality of data frames. In some embodiments, determination unit 520 may generate a plurality of PET images of the scan region corresponding to the plurality of data frames in advance, and a PET image may be generated based on a data frame. The motion curve of the scan region may then be obtained based on the plurality of PET images corresponding to the plurality of data frames by determination unit 520. In some embodiments, the motion curve of the scan region may include a motion curve of a center of mass of a certain organ including, for example, the heart, of a subject. FIG. 8 is an exemplary motion curve of the scan region according to some embodiments of the present disclosure. As shown in FIG. 8, the abscissa may express a time period (e.g., the time period is 1.5 minutes, the unit is the nth 100 microseconds, and n is a positive integer), and the ordinate may express relative positions of the center of mass corresponding to the plurality of PET images of the scan region.

In some embodiments, whether there is a physiological motion in the scan region may be determined based on the motion curve. In some embodiments, determination unit 520 may determine whether there is a physiological motion in the scan region based on the motion curve. Determination unit 520 may determine whether there is a physiological motion in the scan region based on a difference value between a peak value and a valley value within the same time unit (e.g., 100 microseconds). In some embodiments, the length of a time unit may be set by a user (e.g., a doctor) or by the system 100. In some embodiments, the length of a time unit may be selected by a user or the system 100 based on one or more physiological motion of interest corresponding to a subject. For instance, if the physiological motion of interest is the cardiac motion and/or respiratory motion of a human patient, the length of a time unit may be set to be 50 microseconds to 1 second. As another example, if the physiological motion of interest is the cardiac motion and/or respiratory motion of a non-human animal (e.g., a mouse, a rat, a large dog, etc.), the length of a time unit may be set to be 20 microseconds to 1 second. If the difference value is greater than a threshold, determination unit 520 may determine that there is a physiological motion in the scan region. If the difference value is lower than the threshold, determination unit 520 may determine that there is no physiological motion in the scan region. For example, as shown in FIG. 8, in the time unit 500 microseconds to 600 microseconds, point A may indicate a peak value, approximately 126.8, and point B may indicate a valley value, approximately 122.4. The difference value between point A and point B in the time unit 500 microseconds to 600 microseconds is 4.4, which may be greater than a threshold (e.g., the threshold of 2). Under this situation, determination unit 520 may determine that there is a physiological motion in the scan region. In some embodiments, the threshold may be set by a user (e.g., a doctor) or by the system 100. In some embodiments, the threshold may be selected by a user or the system 100 based on one or more physiological motion of interest corresponding to a subject. For instance, if the physiological motion of interest is the cardiac motion and/or respiratory motion of a human patient, the threshold may be set to be 1.3. As another example, if the physiological motion of interest is the cardiac motion and/or respiratory motion of a non-human animal (e.g., a rat, a small dog, a large dog, etc.), the threshold may be set to be 1.

Figure 9:
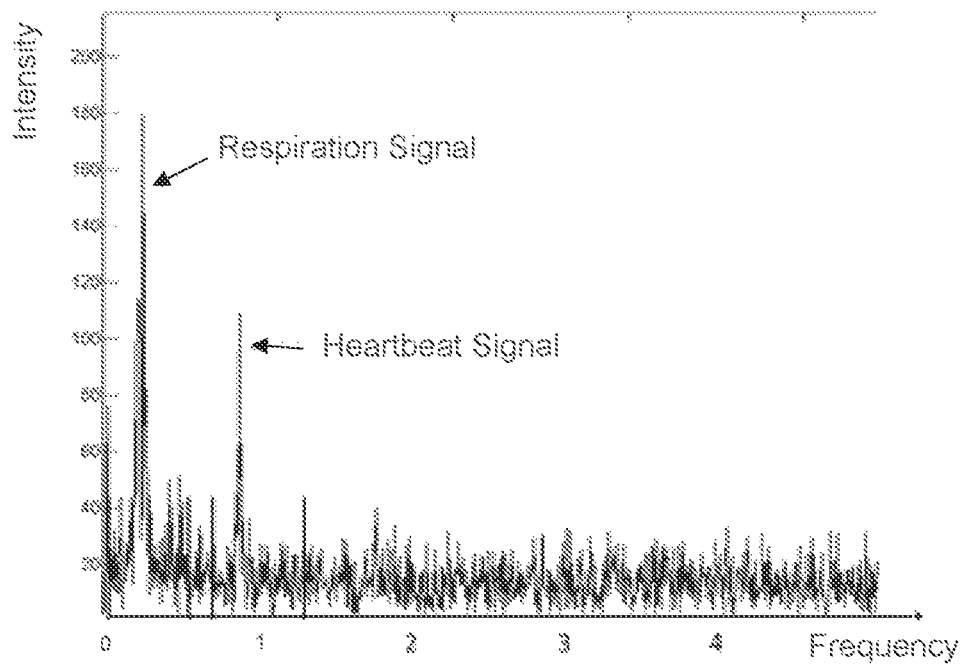
FIG. 9 is a spectrogram corresponding to the motion curve of the scan region as illustrated in FIG. 8.

In 740, a spectrum characteristic corresponding to the motion curve may be obtained. In some embodiments, determination unit 520 may determine the spectrum characteristic corresponding to the motion curve. The spectrum characteristic may include information such as a frequency, signal intensity corresponding to the frequency, or the like, or any combination thereof. In some embodiments, determination unit 520 may generate the spectrum characteristic corresponding to the motion curve based on a spectrogram. The spectrogram may be generated by performing a time domain-frequency domain transform on the motion curve, such as Fourier transform, etc. FIG. 9 is a spectrogram corresponding to the motion curve of the scan region as illustrated in FIG. 8. The spectrogram shown in FIG. 9 is generated by performing Fourier transform on the motion curve of the scan region shown in FIG. 8 by determination unit 520. As shown in FIG. 9, the abscissa may express the frequency (the number of periodic changes in the signal per time unit), and the ordinate may express the signal intensity.

In 750, a physiological motion characteristic may be determined based on the spectrum characteristic. In some embodiments, determination unit 520 may determine the physiological motion characteristic based on the spectrum characteristic. The physiological motion characteristic may indicate what kind of physiological motion exists in a scan region. The physiological motion may include respiration, heartbeat, pulse, or the like, or any combination thereof. For instance, the subject is a human patient; when a target frequency corresponding to the maximum signal intensity is within a normal respiratory frequency range of a human body, determination unit 520 may determine that there is respiratory motion in the scan region. A target frequency may be a frequency corresponding to maximum signal intensity in the spectrogram. As shown in FIG. 9, the target frequency corresponding to the maximum signal intensity (180) is 0.25 Hz, while the normal respiratory frequency range of a human body is between 0.2 Hz and 0.5 Hz. Under this situation, determination unit 520 may determine that there is respiratory motion in the scan region.

Due to individual differences in human bodies, even if the target frequency corresponding to the maximum signal intensity is within the normal respiratory frequency range of a human body, it may unnecessarily indicate that there is respiratory motion in the scan region. In some embodiments, determination unit 520 may include some operations to double check the accuracy of the determination. The following is an example of such a process. Firstly, determination unit 520 may divide the spectrum corresponding to the time period (e.g., 1.5 minutes) collected the first PET data into a first spectrum segment and a second spectrum segment. The first spectrum segment may be a spectrum range (i.e., the normal respiratory frequency range of a human body is between 0.2 Hz and 0.5 Hz) where the target frequency is located. The second spectrum segment may be a spectrum range (i.e., the whole spectrum less the first spectrum segment) where noise is located. Secondly, determination unit 520 may obtain a first intensity value of the first spectrum segment and a second intensity value of the second spectrum segment. Thirdly, determination unit 520 may obtain a first ratio of the first intensity value of the first spectrum segment to the second intensity value of the second spectrum segment. Determination unit 520 may then determine whether the first ratio is greater than a first threshold. If the first ratio is greater than the first threshold, determination unit 520 may determine that there is respiratory motion in the scan region. If the first ratio is not greater than the first threshold, determination unit 520 may determine that there is no respiratory motion in the scan region.

As another example, determination unit 520 may include the following operations to double check the accuracy of the determination. After dividing the spectrum corresponding to the time period (e.g., 1.5 minutes) collected the first PET data into the first spectrum segment and the second spectrum segment, determination unit 520 may obtain the first intensity value of the first spectrum segment and a fifth intensity value of the whole spectrum. Determination unit 520 may obtain a second ratio of the first intensity value of the first spectrum segment to the fifth intensity value of the whole spectrum. Determination unit 520 may then determine that whether the second ratio is greater than a second threshold. If the second ratio is greater than the second threshold, determination unit 520 may determine that there is respiratory motion in the scan region. If the second ratio is not greater than the second threshold, determination unit 520 may determine that there is no respiratory motion in the scan region.

As still another example, determination unit 520 may include the following operations to double check the accuracy of the determination. Firstly, determination unit 520 may divide the spectrum corresponding to the time period (e.g., 1.5 minutes) collected the first PET data into a third spectrum segment and a fourth spectrum segment. The third spectrum segment may be a union of the spectrum range (i.e., the normal respiratory frequency range of a human body is between 0.2 Hz and 0.5 Hz) of the first spectrum segment and a spectrum range where 2 times the target frequency is located. Merely by way of example, when the target frequency is 0.4 Hz, the spectrum range where 2 times the target frequency is located may be set as 0.5 Hz to 1.0 Hz. The third spectrum segment may then include a spectrum range between 0.2 Hz and 1.0 Hz. The fourth spectrum segment may include a spectrum range (i.e., the whole spectrum less the third spectrum segment) where noise is located. Secondly, determination unit 520 may obtain a third intensity value of the third spectrum segment and a fourth intensity value of the fourth spectrum segment. Thirdly, determination unit 520 may obtain a third ratio of the third intensity value of the third spectrum segment to the fourth intensity value of the fourth spectrum segment. Determination unit 520 may then determine that whether the third ratio is greater than a third threshold. If the third ratio is greater than the third threshold, determination unit 520 may determine that there is respiratory motion in the scan region. If the third ratio is not greater than the third threshold, determination unit 520 may determine that there is no respiratory motion in the scan region.

As a further example, determination unit 520 may also obtain a fourth ratio of the third intensity value of the third spectrum segment to the fifth intensity value of the whole spectrum. Determination unit 520 may then determine whether there is respiratory motion in the scan region based on the fourth ratio. If the fourth ratio is greater than a fourth threshold, determination unit 520 may determine that there is respiratory motion in the scan region. If the fourth ratio is not greater than the fourth threshold, determination unit 520 may determine that there is no respiratory motion in the scan region.

It should be noted that the above descriptions of process 700 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, process 700 may include one or more other operations. However, those variations and modifications also fall within the scope of the present disclosure.

Figure 10:
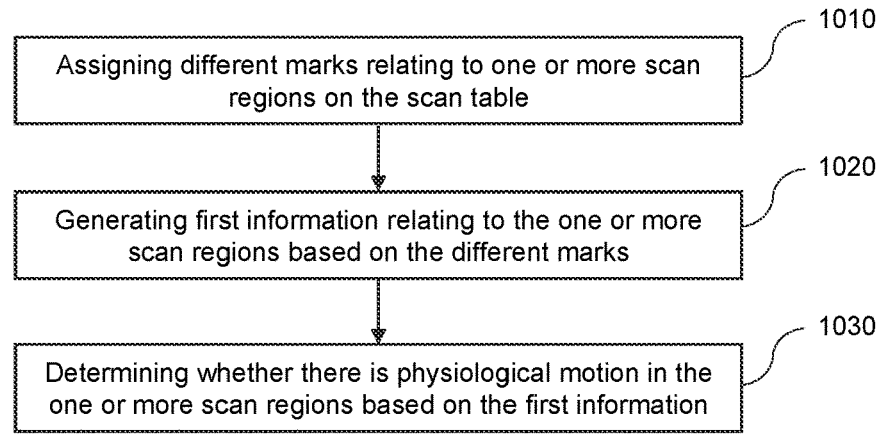
FIG. 10 is a flowchart illustrating an exemplary process for determining whether there is a physiological motion in the one or more scan regions according to some embodiments of the present disclosure.

FIG. 10 is a flowchart illustrating an exemplary process for determining whether there is physiological motion in the one or more scan regions according to some embodiments of the present disclosure. Process 1000, or a portion thereof, may be implemented on a computing device as illustrated in FIG. 2 or a mobile device illustrated in FIG. 3. For illustration purposes, the following description is provided with reference to process 600 as illustrated in FIG. 6. Process 1000 is an exemplary process for achieving 630 of process 600.

Figure 11:
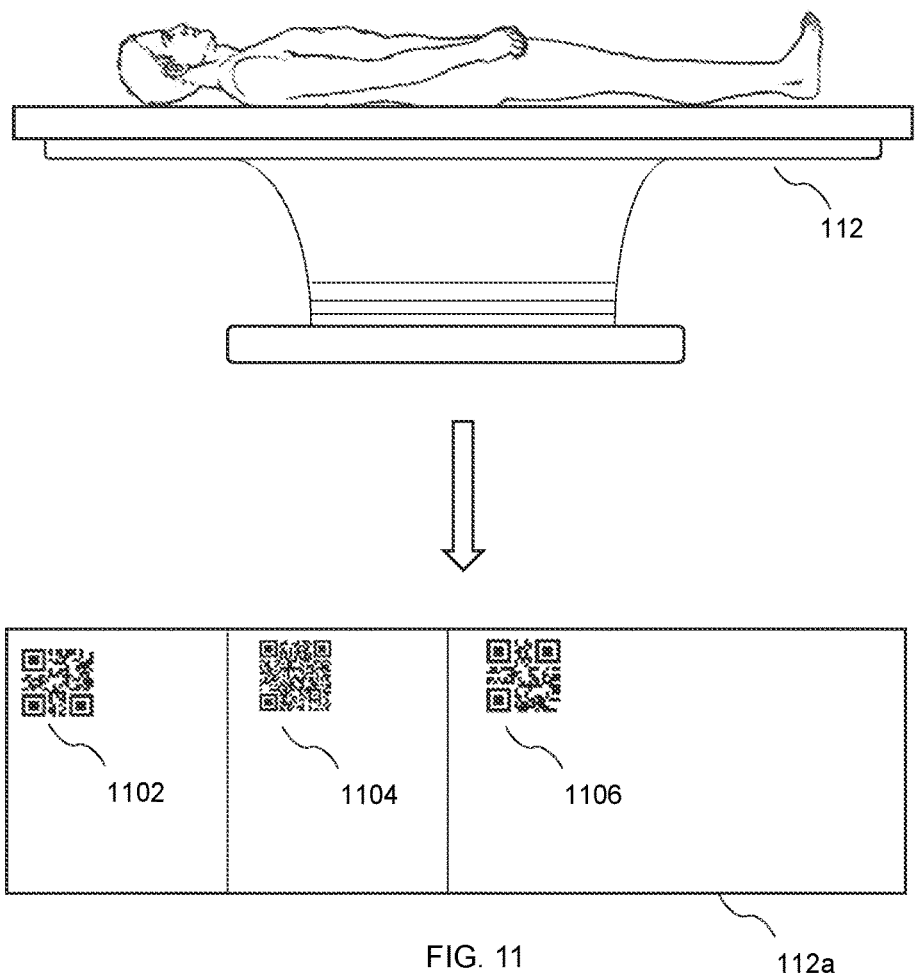
FIG. 11 is a schematic diagram for illustrating process 1000 according to some embodiments of the present disclosure.

In 1010, different marks relating to one or more scan regions may be made on scan table 112. In some embodiments, determination unit 520 may recognize different marks relating to one or more scan regions on scan table 112. The different marks relating to the one or more scan regions may be made on scan table 112 in any one of various ways, such as pasting, printing, etc. A mark may include a serial number, a QR code, a barcode, or the like, or any combination thereof. FIG. 11 is a schematic diagram for illustrating process 1000. Merely by way of example, as shown in FIG. 11, area 112a may include a scan volume of a patient while the patient is lying on table 112. The area 112a may be smaller or equal to the area of the scan table 112. Further, a QR code 1102 may be assigned to a first scan region of scan table 112, a QR code 1104 may be assigned to a second scan region of scan table 112, and a QR code 1106 may be assigned to a third scan region of scan table 112.

In some embodiments, the QR code 1102 may be set to indicate that the head portion of the patient may be in the first scan region, the QR code 1104 may be set to indicate that the chest and abdomen portion of the patient may be in the second scan region, and the QR code 1106 may be set to indicate that the legs portion of the patient may be in the third scan region. In some embodiments, because there is no physiological motion in the head and legs portions of the patient, the QR code 1102 may be same as the QR code 1106 indicating that there is no physiological motion in the corresponding scan region. The QR code 1104 may be different from the QR code 1102 and the QR code 1106, which may indicate that there is physiological motion (e.g., respiration, etc.) in the corresponding scan region. In some embodiments, the QR code 1102 may be different from the QR code 1106 as long as determination unit 520 recognizes each.

In 1020, first information relating to the one or more scan regions may be generated based on the different marks. In some embodiments, determination unit 520 may obtain the first information from a camera. The camera may identify the different marks to generate the first information relating to the one or more scan regions through various image identification techniques. Exemplary image identification techniques may include a neural network based image identification technique, a wavelet moment based image identification technique, a fractal feature-based image identification technique, etc. In some embodiments, the camera may identify the position information of scan table 112 based on the mark, and determination unit 520 may determine the first information based on the position information of scan table 112.

In some embodiments, the first information may be an indication of which part of a patient is located within a scan region. The first information relating to the scan region may be generated by identifying a mark corresponding to the scan region. For example, by identifying the QR code 1102, the first information relating to the first scan region may be that the head portion of the patient is in the first scan region. Similarly, by identifying the QR code 1104 and the QR code 1106, respectively, the first information relating to the second scan region may be that the chest and abdomen portion of the patient may be in the second scan region, the first information relating to the third scan region may be that the legs portion of the patient may be in the third scan region.

In some embodiments, the first information may be a signal (e.g., 0, 1, etc.) that may indicate whether there is physiological motion in a scan region. For example, by identifying the QR code 1102 and the QR code 1106, the first information relating to the corresponding scan region (i.e., the first scan region and the third scan region) may be 0 indicating that there is no physiological motion in the corresponding scan region. By identifying the QR code 1104, the first information relating to the corresponding scan region (i.e., the second scan region) may be 1 indicating that there is physiological motion (e.g., respiration, etc.) in the corresponding scan region.

In 1030, a determination may be made as to whether there is physiological motion in the one or more scan regions based on the first information. In some embodiments, determination unit 520 may determine whether there is physiological motion in the one or more scan regions based on the first information. For example, after determination unit 520 obtains first information relating to a scan region, determination unit 520 may determine whether there is physiological motion in the scan region based on the indication of which body part of the patient is contained in the scan region. If the scan region only contains the head and/or legs of the patient, determination unit 520 may determine there is no physiological motion in the scan region. If the scan region contains the lungs or part of the lungs, determination unit 520 may determine there is physiological motion (e.g., respiration, etc.) in the scan region.

As another example, after determination unit 520 obtains first information relating to a scan region, determination unit 520 may determine whether there is physiological motion in the scan region based on the signal (e.g., 0, 1, etc.) indicating whether there is physiological motion in the scan region. If the signal obtained by determination unit 520 is 0, determination unit 520 may determine there is no physiological motion in the scan region. If the signal obtained by determination unit 520 is 1, determination unit 520 may determine there is physiological motion (e.g., respiration, heartbeat, etc.) in the scan region.

It should be noted that the above descriptions of process 1000 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, process 1000 may include one or more other operations. However, those variations and modifications also fall within the scope of the present disclosure.

Figure 12:
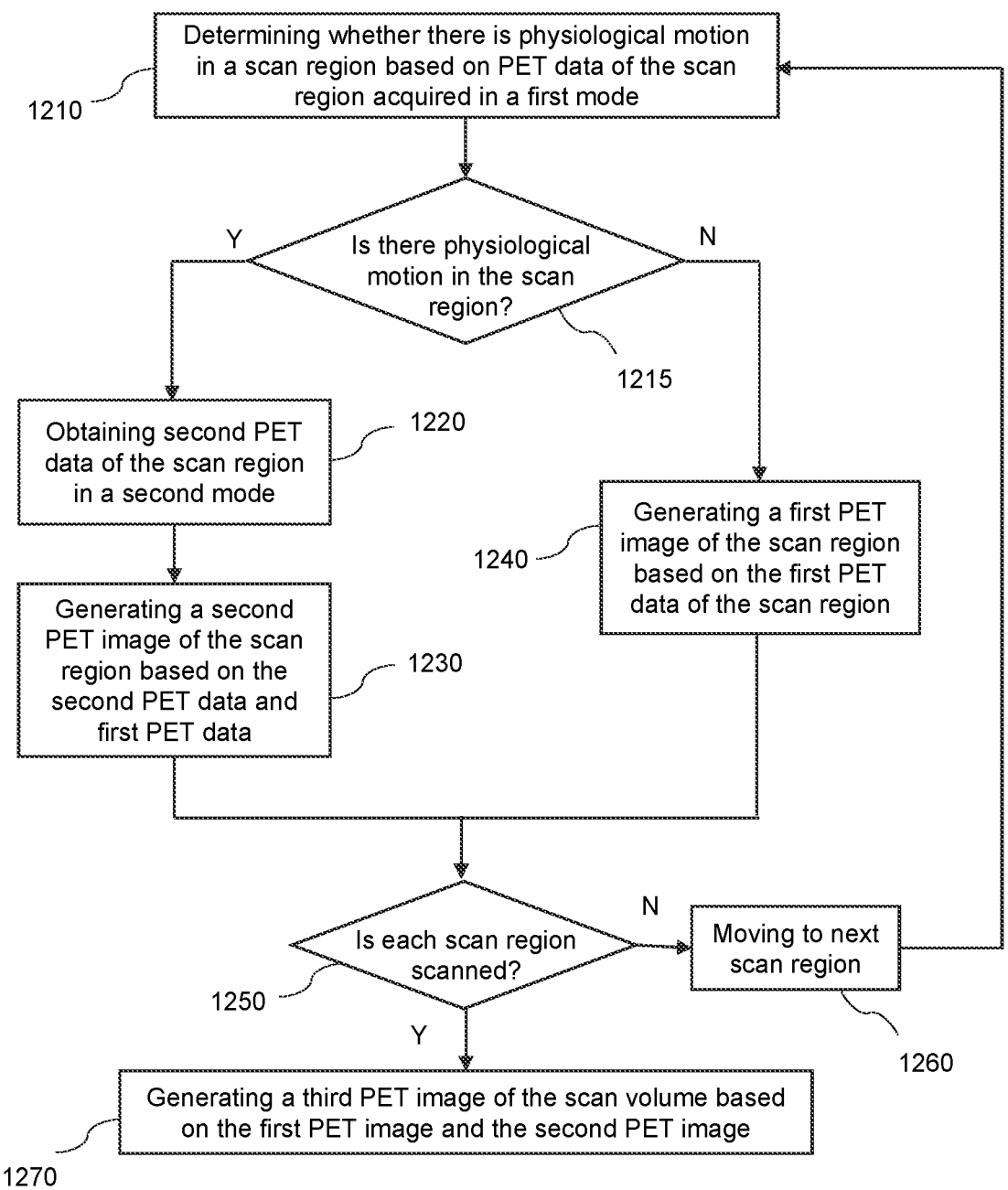
FIG. 12 is a flowchart illustrating an exemplary process for generating a PET image of a scan volume according to some embodiments of the present disclosure.

FIG. 12 is a flowchart illustrating an exemplary process for generating a PET image of the scan volume according to some embodiments of the present disclosure. Process 1200, or a portion thereof, may be implemented on a computing device as illustrated in FIG. 2 or a mobile device illustrated in FIG. 3. For illustration purposes, the following description is provided with reference to the imaging system 100 as illustrated in FIG. 1. Process 1200 is an exemplary process for achieving 680 of process 600.

In 1210, a determination may be made as to whether there is physiological motion in a scan region based on first PET data of the scan region acquired in a first mode. In some embodiments, determination unit 520 may determine whether there is physiological motion in the scan region based on first PET data of the scan region acquired in the first mode. Acquisition module 420 may obtain the first PET data of the scan region in the first mode in advance. The first mode may include the static mode, the transmission mode, or the like, or any combination thereof. Descriptions of how to determine whether there is physiological motion in the scan region based on the first PET data of the scan region acquired in the first mode may be found in FIG. 7, and descriptions thereof. The first PET data of the scan region acquired in the first mode may be stored in storage module 430.

In 1215, in response to the determination that there is physiological motion in the scan region, process 1200 may proceed to 1220. In response to the determination that there is no physiological motion in the scan region, process 1200 may proceed to 1240.

In 1220, second PET data of the scan region may be obtained in a second mode. In some embodiments, when determination unit 520 determines that there is physiological motion in the scan region, acquisition module 420 may acquire the second PET data of the scan region in the second mode. The second mode may include the gating mode, etc. The second PET data of the scan region acquired in the second mode may be stored in storage module 430.

In 1230, a PET sub-image of the scan region may be generated based on the second PET data and the first PET data. In some embodiments, when determination unit 520 determines that there is physiological motion in the scan region, reconstruction unit 530 may reconstruct the PET sub-image of the scan region based on the second PET data of the scan region and the first PET data of the scan region, which may improve data utilization and save time of collecting the second PET data in the second mode. Exemplary reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, reconstruction unit 530 may also include performing data reorganization on the second PET data of the scan region and the first PET data of the scan region.

In 1240, a PET sub-image of the scan region may be generated based on the first PET data of the scan region. In some embodiments, when determination unit 520 determines that there is no physiological motion in the scan region, reconstruction unit 530 may reconstruct the PET sub-image of the scan region based on the first PET data of the scan region. Exemplary reconstruction technique may include a static reconstruction technique, etc.

In 1250, when there is a scan region yet to be scanned, process 1200 may proceed to 1260. When each scan region of the one or more scan regions is scanned, process 1200 may proceed to 1270. In some embodiments, control module 410 may determine whether there is a scan region yet to be scanned. For example, control module 410 may count the scan region(s) that has/have been scanner. Control module 410 may continue scanning until the number of the scanned scan region(s) reaches the threshold (i.e., the number of scan regions divided by division unit 510, such as 3).

In 1260, a next scan region may be moved into detection region 113. In some embodiments, control module 410 may move scan table 112 to a next table position; the next scan region may then be moved into detection region 113. Processing device 140 (e.g., processing module 440) may cause operations 1210 to 1250 to be repeated on the next scan region.

In 1270, a PET image of the scan volume may be generated based on one or more PET sub-images. In some embodiments, stitching unit 540 may generate the PET image of the scan volume by stitching the one or more PET sub-images. Exemplary image stitching techniques may include a frequency domain based technique (phase correlation technique), or a time domain based technique, or the like. In some embodiments, stitching unit 540 may use different image stitching algorithms including a Fourier phase correlation algorithm, a point-registration algorithm, an intensity-based algorithm, etc.

In some embodiments, the PET image of the scan volume may be generated by performing one-time stitching after all of the one or more PET sub-images are obtained. In some embodiments, operation 1270 may be performed before operation 1250. After each of the one or more PET sub-images is obtained, an image stitching operation may be performed based on the newly generated PET sub-image and the stitched PET sub-image already generated. Specifically, except for a first PET sub-image corresponding to a first scan region, any subsequent PET sub-image may be stitched with the PET sub-images already obtained. The PET image of the scan volume may be obtained after every scan region is scanned.

In should be noted that the above descriptions of process 1200 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, process 1200 may include an operation for reconstruction post-processing before the stitching of the one or more PET sub-images. In some embodiments, process 1200 may include an operation for image stitching pre-processing before the stitching of the one or more PET sub-images. In some embodiments, process 1200 may be an operation for setting a collection parameter before PET data collection of a scan region. However, those variations and modifications also fall within the scope of the present disclosure.

Figure 13:
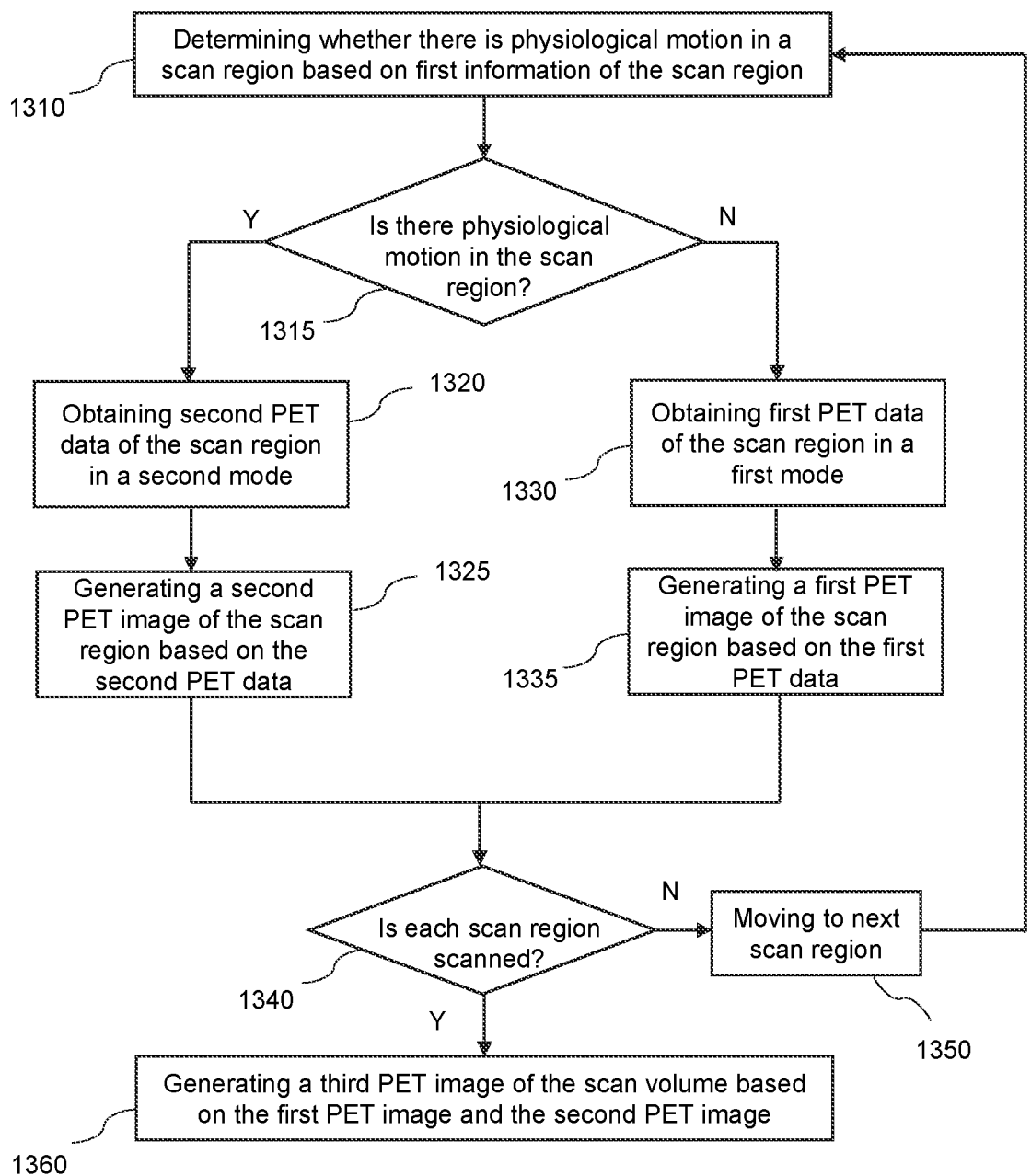
FIG. 13 is flowchart illustrating another exemplary process for generating a PET image of a scan volume according to some embodiments of the present disclosure; and, FIG. 14 is a schematic diagram illustrating an exemplary PET imaging system according to some embodiments of the present disclosure.

FIG. 13 is a flowchart illustrating an exemplary process for generating a PET image of the scan volume according to some embodiments of the present disclosure. Process 1300, or a portion thereof, may be implemented on a computing device as illustrated in FIG. 2 or a mobile device illustrated in FIG. 3. For illustration purposes, the following description is provided with reference to the imaging system 100 as illustrated in FIG. 1.

In 1310, a determination may be made as to whether there is physiological motion in a scan region based on first information of the scan region. In some embodiments, determination unit 520 may determine whether there is physiological motion in the scan region based on the first information of the scan region. In some embodiments, merely by way of example with reference to a patient, the first information may be an indication of which body part of a patient is contained in the scan region. In some embodiments, the first information may be a signal (e.g., 0, 1, etc.) that may indicate whether there is physiological motion in the scan region. The first information relating to the scan region may be generated by identifying a mark corresponding to the scan region, analyzing a topogram of the patient, an external device (e.g., a vital signs monitor, etc.), or the like, or any combination thereof. Related descriptions may be found anywhere else in the present disclosure. See, e.g., relevant description in connection with FIG. 6.

In 1315, in response to the determination that there is physiological motion in the scan region, process 1300 may proceed to 1320. In response to the determination that there is no physiological motion in the scan region, process 1300 may proceed to 1330.

In 1320, second PET data of the scan region may be obtained in a second mode. In some embodiments, when determination unit 520 determines that there is physiological motion in the scan region, acquisition module 420 may acquire the second PET data of the scan region in the second mode. The second mode may include the gating mode, etc. The second PET data of the scan region acquired in the second mode may be stored in storage module 430.

In 1325, a PET sub-image of the scan region may be generated based on the second PET data of the scan region. In some embodiments, when determination unit 520 determines that there is physiological motion in the scan region, reconstruction unit 530 may reconstruct the PET sub-image of the scan region based on the second PET data of the scan region. Exemplary reconstruction techniques may include VSM gating reconstruction, digital gating reconstruction, etc.

In 1330, first PET data of the scan region may be obtained in a first mode. In some embodiments, when determination unit 520 determines that there is no physiological motion in the scan region, acquisition module 420 may acquire the first PET data of the scan region in the first mode. The first mode may include the static mode, the transmission mode, or the like, or any combination thereof. The first PET data of the scan region acquired in the first mode may be stored in storage module 430.

In 1335, a PET sub-image of the scan region may be generated based on the first PET data. In some embodiments, when determination unit 520 determines that there is no physiological motion in the scan region, reconstruction unit 530 may reconstruct the PET sub-image of the scan region based on the first PET data of the scan region. Exemplary reconstruction techniques may include a static reconstruction technique, etc.

In 1340, when there is a scan region yet to be scanned, process 1300 may proceed to 1350. When each scan region of the one or more scan regions is scanned, process 1300 may proceed to 1360. In some embodiments, control module 410 may determine whether there is a scan region left to be scanned. For example, control module 410 may count scanned scan region(s). Control module 410 may continue scanning until the number of the scanned scan region(s) reaches the threshold (i.e., the number of scan regions divided by division unit 510, such as 3).

In 1350, a next scan region may be moved into detection region 113. In some embodiments, control module 410 may move scan table 112 to a next table position; the next scan region may then be moved into detection region 113. Processing device 140 (e.g., processing module 440) may cause operations 1310 to 1340 to be repeated on the next scan region.

In 1360, a PET image of the scan volume may be generated based on one or more PET sub-images. In some embodiments, stitching unit 540 may generate the PET image of the scan volume by stitching the one or more PET sub-images. Exemplary image stitching techniques may include a frequency domain based technique (phase correlation technique), or a time domain based technique, or the like. In some embodiments, stitching unit 540 may use different image stitching algorithms including a Fourier phase correlation algorithm, a point-registration algorithm, an intensity-based algorithm, etc.

In some embodiments, the PET image of the scan volume may be generated by performing one-time stitching after all of the one or more PET sub-images are obtained. In some embodiments, operation 1360 may be performed before operation 1340. After each of the one or more PET sub-images is obtained, an image stitching operation may be performed. Specifically, except for a first PET sub-image corresponding to a first scan region, any subsequent PET sub-image may be stitched with the PET sub-images already obtained. The PET image of the scan volume may be obtained after every scan region is scanned. It should be noted that the above descriptions of process 1300 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, process 1300 may include an operation for reconstruction post-processing before stitching the one or more PET sub-images. In some embodiments, process 1300 may include an operation for image stitching pre-processing before the stitching of the one or more PET sub-images. In some embodiments, process 1300 may be an operation for setting a collection parameter before PET data collection of a scan region. However, those variations and modifications also fall within the scope of the present disclosure.

Figure 14:
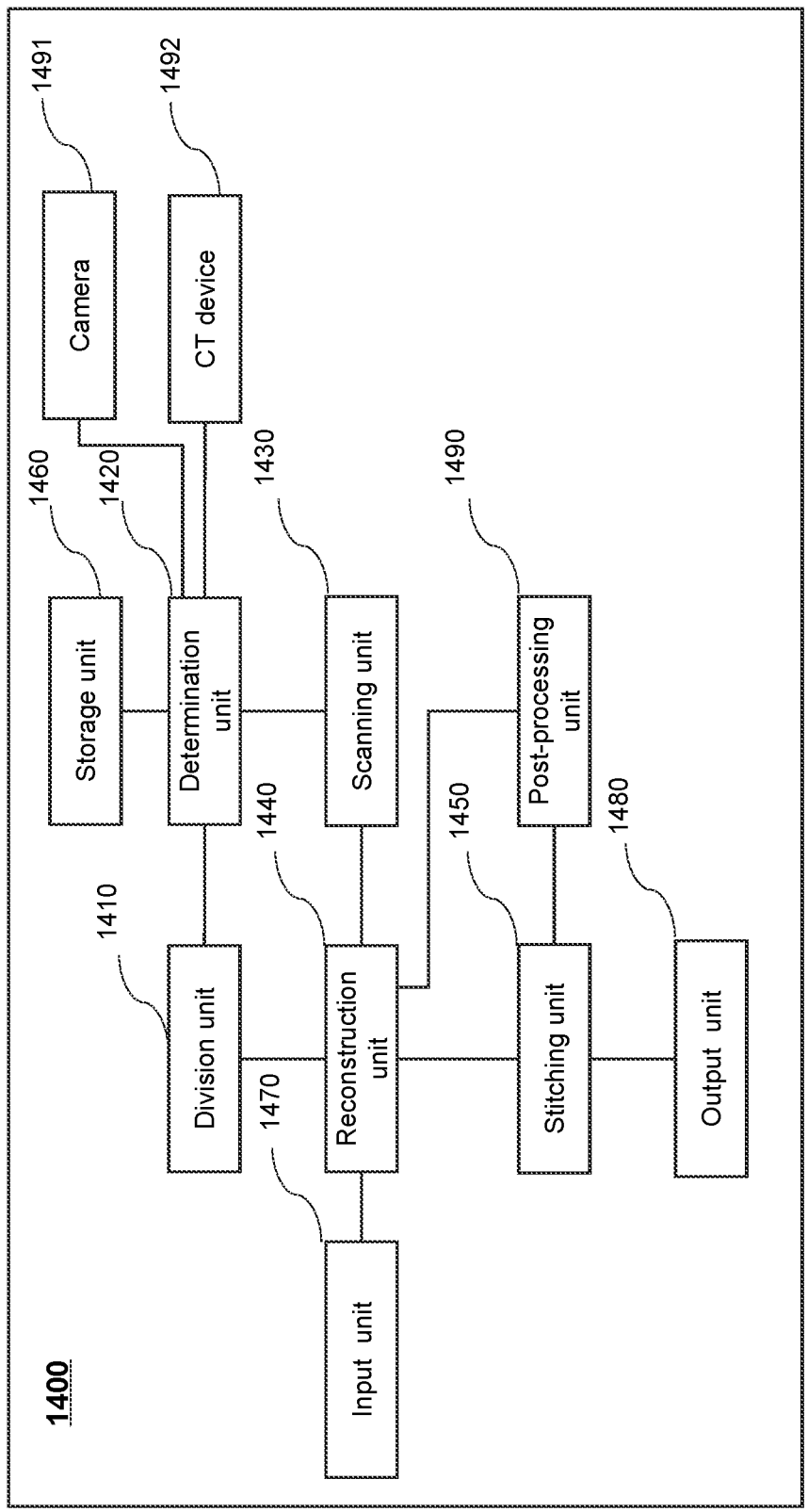

FIG. 14 is a schematic diagram illustrating an exemplary PET imaging system 1400 according to some embodiments of the present disclosure. For illustration purposes, as shown in FIG. 14, PET imaging system 1400 may include division unit 1410, determination unit 1420, scanning unit 1430, reconstruction unit 1440, stitching unit 1450, storage unit 1460, input unit 1470, output unit 1480, post-processing unit 1490, camera 1491, and CT device 1492.

Division unit 1410 may divide a scan volume of a subject into one or more scan regions. Determination unit 1420 may, for each scan region of the one or more scan regions, determine whether there is physiological motion in the scan region. Scanning unit 1430 may obtain PET data based on the determination of the determination unit 1420. For example, in response to a determination performed by determination unit 1420 that there is no physiological motion in the scan region, scanning unit 1430 may then, for the scan region, perform data collection in a first mode. The first mode may include the static mode, the transmission mode, or the like, or any combination thereof. As another example, in response to a determination performed by determination unit determination unit 1420 that there is physiological motion (e.g., respiration, heartbeat, etc.) in the scan region, scanning unit 1430 may then, for the scan region, perform data collection in a second mode. The second mode may include the gating mode, etc.

In some embodiments, when determination unit 1420 determines that there is physiological motion in the scan region, reconstruction unit 1440 may reconstruct the PET sub-image of the scan region based on the second PET data of the scan region. Exemplary reconstruction techniques may include VSM gating reconstruction, digital gating reconstruction, etc. In some embodiments, when determination unit 1420 determines that there is no physiological motion in the scan region, reconstruction unit 1440 may reconstruct the PET sub-image of the scan region based on the first PET data of the scan region. Exemplary reconstruction techniques may include a static reconstruction technique, etc.

Stitching unit 1450 may obtain a PET image of the scan volume by stitching PET sub-images of the one or more scan regions. Stitching unit 1450 may employ different kinds of imaging stitching techniques for stitching the PET sub-images. Exemplary image stitching techniques may include a frequency domain based technique (phase correlation technique), or a time domain based technique, or the like. In some embodiments, stitching unit 1450 may use different image stitching algorithms including a Fourier phase correlation algorithm, a point-registration algorithm, an intensity based algorithm, etc. Post-processing unit 1490 may post process the image generated by the reconstruction unit 1440, and send the post processed image to the stitching unit 1450.

In some embodiments, stitching unit 1450 may include, before the stitching procedure, adjusting a weight ratio and smoothing coefficient of an overlapped part formed by a static reconstructed PET sub-image and a gating reconstructed PET sub-image. Image quality of the overlapped part during the stitching procedure may be improved. Storage unit 1460 may store relationship between different marks and scan regions. In some embodiments, determination unit 1420 may recognize different marks relating to one or more scan regions on scan table 112. Input unit 1470 and output unit 1480 may input and/or output signals, data, information, etc. In some embodiments, input unit 1470 and output unit 1480 may enable user interaction with PET imaging system 1400. In some embodiments, input unit 1470 and output unit 1480 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. The output unit 1480 may output image in digital imaging and communications in medicine (DICOM) form. The CT device 1492 may obtain topogram of a scan region of a patient. In some embodiments, determination unit 1420 may determine whether there is physiological motion in a scan region based on a topogram of the subject. Camera 1491 may a photograph of the subject of a scan region. In some embodiments, the camera may identify different marks of scan table 112 through various image identification techniques to determine whether the scan region could have physiological motion. In some embodiments, the camera may identify the position of the scan table 112 to determine whether the scan region could have physiological motion.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one machine each of which has at least one processor and a storage device, the method comprising:
   obtaining a motion curve of a portion of a subject in at least one scan region of the subject;
   determining a spectrum corresponding to the motion curve;
   dividing the spectrum into a plurality of spectrum segments, wherein the plurality of spectrum segments include a first spectrum segment, and the first spectrum segment includes a union of a spectrum range where a target frequency is located and a spectrum range where 2 times the target frequency is located, wherein the plurality of spectrum segments include a second spectrum segment, the second spectrum segment includes a spectrum range where a noise is located;
   determining whether there is a physiological motion in the at least one scan region based on a first intensity value of the first spectrum segment by obtaining a ratio of the first intensity value of the first spectrum segment to a third intensity value of the second spectrum segment; and determining whether there is a physiological motion in the at least one scan region based on the ratio;
   determining a scan mode for scanning the at least one scan region based on whether there is the physiological motion in the at least one scan region; and
   generating at least one PET sub-image of the at least one scan region based on PET data of the at least one scan region acquired in the scan mode.

2. The method of claim 1, wherein
   the scan mode includes a first mode if it is determined that there is no physiological motion in the at least one scan region, and
   the first mode includes at least a static mode or a transmission mode for scanning the at least one scan region.

3. The method of claim 1, wherein
   the scan mode includes a second mode if it is determined that there is the physiological motion in the at least one scan region, and
   the second mode includes a gating mode for scanning the at least one scan region.

4. The method of claim 1, wherein the obtaining a motion curve of a portion of a subject in at least one scan region of the subject comprises:
   obtaining reference PET data of the at least one scan region acquired in a first mode or in a second mode;
   dividing the reference PET data of the at least one scan region into a plurality of data frames; and
   obtaining the motion curve based on the plurality of data frames.

5. The method of claim 1, wherein the method further comprises:
   determining a scan volume of the subject supported by a scan table; and
   dividing the scan volume into the at least one scan region, wherein each of the at least one scan region corresponds to a table position.

6. The method of claim 5, further comprising:
   adjusting a statistical characteristic of the at least one scan region according to at least one table position corresponding to the at least one scan region, wherein the statistical characteristic of one of the at least one scan region includes at least one of a scan time period of the scan region, a scan velocity of the scan region, or a number of data frames of the scan region.

7. The method of claim 5, further comprising:
   generating a PET image of the scan volume by stitching the at least one PET sub-image of the at least one scan region.

* * * * *